(12) United States Patent
Fucikova et al.

(10) Patent No.: US 9,562,219 B2
(45) Date of Patent: Feb. 7, 2017

(54) CRYOPRESERVATION OF APOPTOTIC CANCER CELLS FOR USE IN IMMUNOTHERAPY AGAINST CANCER

(71) Applicant: SOTIO a.s., Prague (CZ)

(72) Inventors: Jitka Fucikova, Jihlava (CZ); Lenka Koci, Brno (CZ); Katerina Pokorna, Prague (CZ); Iva Truxova, Olomouc (CZ); Irena Moserova, Prague (CZ); Daniela Rozkova, Prague (CZ); Radek Spisek, Prague (CZ)

(73) Assignee: SOTIO A.S., Prague (CZ)

( * ) Notice: Subject to any disclaimer, the term of this patent is extended or adjusted under 35 U.S.C. 154(b) by 39 days.

(21) Appl. No.: 14/142,448

(22) Filed: Dec. 27, 2013

(65) Prior Publication Data
US 2015/0184130 A1 Jul. 2, 2015

(51) Int. Cl.
| | | |
|---|---|---|
| C12N 5/09 | (2010.01) | |
| A61K 35/13 | (2015.01) | |
| A61K 39/00 | (2006.01) | |
| A01N 1/02 | (2006.01) | |

(52) U.S. Cl.
CPC ............ *C12N 5/0693* (2013.01); *A01N 1/0221* (2013.01); *A01N 1/0278* (2013.01); *A61K 35/13* (2013.01); *A61K 39/0011* (2013.01); *A61K 2039/5152* (2013.01)

(58) Field of Classification Search
None
See application file for complete search history.

(56) References Cited

U.S. PATENT DOCUMENTS

| | | | |
|---|---|---|---|
| 2002/0146396 | A1 | 10/2002 | Albert et al. |
| 2008/0286314 | A1 | 11/2008 | Palucka et al. |
| 2013/0011438 | A1 | 1/2013 | Bartunková et al. |
| 2014/0086957 | A1 | 3/2014 | Bartunková et al. |

FOREIGN PATENT DOCUMENTS

| | | | |
|---|---|---|---|
| EP | 2543386 A1 | | 1/2013 |
| WO | WO99/58645 | * | 11/1999 |
| WO | WO 2006/095330 A2 | | 9/2006 |
| WO | WO2013/004708 | * | 1/2013 |
| WO | WO 2013/004708 A1 | | 1/2013 |
| WO | WO 2015/097037 A1 | | 7/2015 |

OTHER PUBLICATIONS

The abstract of Shen et al (Zhonghua Laonian Yixue Zazhi, 2011, vol. 30, pp. 742-745).*
Freshney (The Culture of Animal Cells, 1994, pp. 255-260).*
Ali and Olivo (International Journal of Oncology, 2002, vol. 21, pp. 531-540).*
Zitvogel et al (Clinical Cancer Research, 2010, vol. 16, pp. 3100-3104).*
Obeid et al (Nature Medicine, 2007, vol. 13, pp. 54-61).*
Obeid et al (Nature Medicine, 2007, vol. 13, supplemental Figure 3.*
"Active cellular immunotherapy of cancer using dendritic cells", Sotio, [Internet], Nov. 29, 2013 [retrieved on Feb. 27, 2015], Retrieved from the Internet <URL: https://web.archive.org/web/20131129093448/http://www.sotio.com/research/active-cellular-immunotherapy>.
Alaniz, et al., "Pulsing dendritic cells with whole tumor cell lysates", Cancer Vaccines: Methods and Protocols, Methods Mol. Biol., Michael J.P. Lawman and Patricia D. Lawman (eds.), New York, New York, Springer Science and Business Media, 2014, vol. 1139: 27-31.
Banchereau and Steinman, "Dendritic cells and the control of immunity", Nature, 1998, vol. 392(6673): 245-252.
Banchereau, et al., "Dendritic cells as vectors for therapy", Cell, 2001, vol. 106(3): 271-274.
Banchereau, et al., "Immunobiology of dendritic cells", Annu. Rev. Immunol., 2000, vol. 18: 767-811.
Berger, et al., "Large-scale generation of mature monocyte-derived dendritic cells for clinical application in cell factories", J. Immunol. Methods, 2002, vol. 268(2): 131-140.
Butterfield, L., "Dendritic cells in cancer immunotherapy clinical trials: are we making progress?", Front Immunol., 2013, vol. 4: 454 (pp. 1-7).
Casares, et al., "Caspase-dependent immunogenicity of doxorubicin-induced tumor cell death", J. Exp. Med. 2005, vol. 202(12): 1691-1701.
Chen, et al. "Shikonin induces immongenic cell death in tumor cells and enhances dendritic cell-based cancer vaccine", Cancer Immunol. Immunother., 2012, vol. 61(11): 1989-2002.
Chiang, et al.,"Adjuvants for enhancing the immunogenicity of whole tumor cell vaccines", Int. Rev. Immunol., 2011, vol. 30(2-3): 150-182.
Diehl, et al., "Induction of tumor cell death by high hydrostatic pressure as a novel supporting technique in orthopedic surgery", Oncol. Rep., 2003, vol. 10(6): 1851-1855.
Dubsky, et al., "Human dendritic cell subsets for vaccination", J. Clin. Immunol., 2005, vol. 25(6): 551-572.
Dudek, et al., "Inducers of immunogenic cancer cell death", Cytokine Growth Factor Rev., 2013, vol. 24(4): 319-333.
Dumitriu, et al., "The secretion of HMGB1 is required for the migration of maturing dendritic cells", J. Leukoc. Biol., 2007, vol. 81(1): 84-91.

(Continued)

*Primary Examiner* — Karen Canella
(74) *Attorney, Agent, or Firm* — Leason Ellis LLP.

(57) ABSTRACT

Described herein is a reliable method for preparing a potent vaccine useful for immunotherapy comprising the step of cryopreserving a population of cells undergoing immunogenic cell death, and using such cells to activate dendritic cells for use in immunotherapy. In a specific embodiment, the method comprises cryopreserving cancer cells undergoing cell death, which can be used to prepare a pharmaceutical composition for immunotherapy against cancer.

45 Claims, 11 Drawing Sheets

(56) References Cited

OTHER PUBLICATIONS

Figure 1A:
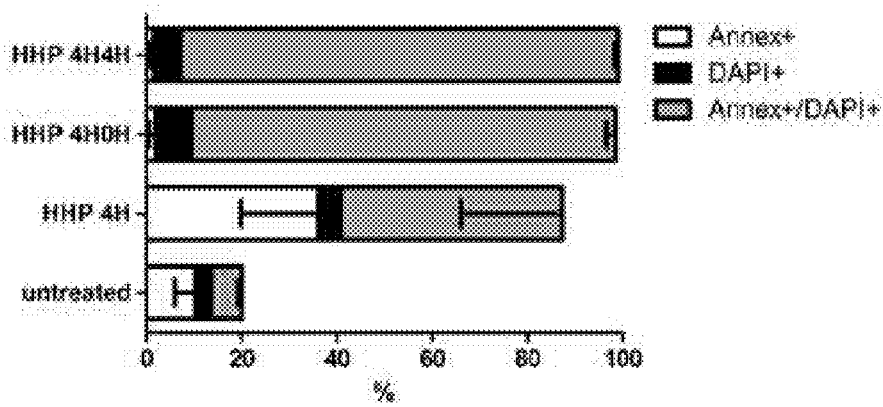
Figure 1A:
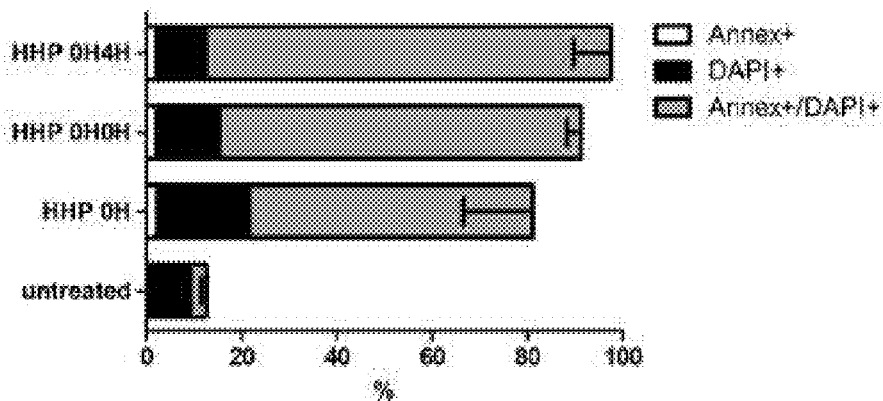

Feuerstein, et al., "A method for the production of cryopreserved aliquots of antigen-preloaded, mature dendritic cells ready for clinical use", J. Immunol. Methods, 2000, vol. 245(1-2): 15-29.
Fialova, et al. "Dynamics of T-cell infiltration during the course of ovarian cancer: The gradual shift from Th17 effector cell response to a predominant infiltration by regulatory T-cells", Int. J. Cancer, 2013, vol. 132(5); 1070-1079.
Frank, et al. "Harnessing naturally occurring tumor immunity: a clinical vaccine trial in prostate cancer", PLoS One, vol. 5(9), 2010, p. E12367.
Fucikova, et al., "High hydrostatic pressure induces immunogenic cell death in human tumor cells", Int. J. Cancer., 2014, vol. 135(5): 1165-1177.
Fucikova, et al., "High hydrostatic pressure induces immunogenic cell death in human tumor cells." Poster presented at: ASCO Annual '13 Meeting; 49th Annual Meeting of the American Society for Clinical Oncology; May 31-Jun. 4, 2013; Chicago, IL.
Fucikova, et al., "Human tumor cells killed by anthracyclines induce a tumor-specific immune response", Cancer Res., 2011, vol. 71(14): 4821-4833.
Fucikova, et al., "Poly I: C-activated dendritic cells that were generated in CellGro for use in cancer immunotherapy trials", J. of Transl. Med., 2011, vol. 9(223): 1-10.
Galluzzi and Kroemer, "The grand challenges to cellular and molecular oncology", Front. in Oncol., 2011, vol. 1: 2 (p. 1).
Gameiro, et al., "Radiation-induced immunogenic modulation of tumor enhances antigen processing and calreticulin exposure, resulting in enhanced T-cell killing", Oncotarget, 2014, vol. 5(2): 403-416.
Garg, et al., "Cancer immunogenicity, danger signals, and DAMPs: what, when, and how?" Biofactors, 2013, vol. 39(4): 355-367.
Garg, et al., "A novel pathway combining calreticulin exposure and ATP secretion in immunogenic cancer cell death", Embo. J., 2012, vol. 31(5): 1062-1079.
Garg, et al., "Danger signalling during cancer cell death: origins, plasticity and regulation", Cell Death Differ., 2014, vol. 21(1): 26-38.
Gilboa, E.,"DC-based cancer vaccines", J. Clin. Invest., 2007, vol. 117(5): 1195-1203.
Hingorani, et al., "Detection of apoptosis using the BD annexin V FITC assay on the BD FACSVerse system", BD Biosciences, Application Notes, Aug. 2011: 1-12.
International Preliminary Report on Patentability dated Sep. 10, 2013 of International application No. PCT/EP2012/062950.
International Search Report and Written Opinion dated Sep. 17, 2012 of International application No. PCT/EP2012/062950.
International Search Report and Written Opinion dated Mar. 16, 2015 of International application No. PCT/EP2014/078247.
Inzkirweli et al., "Antigen loading of dendritic cells with apoptotic tumor cell-preparations is superior to that using necrotic cells or tumor lysates", Anticancer Res., 2007, vol. 27(4B): 2121-2129.
John, et al., "Cryopreserved dendritic cells for intratumoral immunotherapy do not require re-culture prior to human vaccination", J. Immunol. Methods, 2005, vol. 299(1-2): 37-46.
Kamarck, M., "Fluorescence-activated cell sorting of hybrid and transfected cells", Methods Enzymol., Sidney P. Colowick and Nathan O. Kaplan (eds.), New York, New York, Academic Press, 1987, vol. 151: 150-165.
Kono, et al., "Immunogenic tumor cell death induced by chemoradiotherapy: molecular mechanisms and a clinical translation", Cell Death Dis., 2013, vol. 4: 688.
Korn, et al., "High hydrostatic pressure inactivated human tumour cells preserve their immunogenicity", Cell. Mol. Biol., 2004, vol. 50(4): 469-477.
Kovalcsik, et al. "Poly(I:C)-induced tumour cell death leads to DC maturation and Th1 activation", Cancer Immunol. Immunother., 2011, vol. 60(11): 1609-1624.
Kroemer, et al., "Immunogenic cell death in cancer therapy", Annu. Rev. of Immunol., 2012, vol. 31: 51-72.
Krysko, et al., "Immunogenic cell death and DAMPs in cancer therapy", Nat. Rev. Cancer, 2012, vol. 12(12): 860-875.
Larsson, et al., "Dendritic cells resurrect antigens from dead cells", Trends Immunol., 2001. vol. 22(3): 141-148.
Liu, et al., "Delivery of whole tumor lysate into dendritic cells for cancer vaccination", Electroporation Protocols: Preclinical and Clinical Gene Medicine, Methods Mol. Biol., S. Li (ed.), Totowa, NJ, Humana Press, 2008, vol. 423: 139-153.
Maltais, et al., "Cryotreatment as a simple method for cell preparation in autologous tumor cell-based vaccination", Int. J. Oncol., 2010, vol. 36(3): 617-622.
Martins, et al., "Molecular mechanisms of ATP secretion during immunogenic cell death", Cell Death Differ., 2014, vol. 21(1): 79-91.
Meijerink, et al., "Cryopreservation of monocytes or differentiated immature DCs leads to an altered cytokine response to TLR agonists and microbial stimulation", J. Immunol. Methods, 2011, vol. 373(1-2): 136-142.
Minárik, et al., "Phase I/II of clinical study of prostate cancer immunotherapy using dendritic cell vaccination strategy—first results", European Urol. Supplements, 2010, vol. 9(6): 629, C40.
Morris, C.B. "Cryopreservation of Animal and Human Cell Lines", Cryopreservation and Freeze-Drying Protocols, Methods in Molecular Biology, J.G. Day and G.N. Stacey (eds.), Totowa, NJ, Humana Press, 2007, vol. 368: 227-236.
Morse, et al., "Dendritic cell maturation in active immunotherapy strategies", Expert Opin. Biol. Ther., 2002, vol. 2(1): 35-43.
Palucka, et al., "Recent developments in cancer vaccines", J. Immunol., 2011, vol. 186(3): 1325-1331.
Richert et al., "Promotion of tumor antigenicity in EL-4 leukemia cells by hydrostatic pressure", Cancer Immunol. Immunother., 1986, vol. 22(2): 119-124.
Rizzo, et al., "Ex vivo loading of autologous dendritic cells with tumor antigens", Cancer Vaccines: Methods and Protocols, Methods Mol. Biol., Michael J.P. Lawman and Patricia D. Lawman (eds.), New York, New York, Springer Science and Business Media, 2014, vol. 1139: 41-44.
Rozkova, et al., "Focus on Focis: combined chemo-immunotherapy for the treatment of hormone-refractory metastatic prostate cancer", Clin. Immunol., 2009, vol. 131(1): 1-10.
Sharma, et al., "γ-Radiation promotes immunological recognition of cancer cells through increased expression of cancer-testis antigens in vitro and in vivo", PloS one, 2011, vol. 6(11): e28217 (1-11).
Sheikh, et al., "Sipuleucel-T immune parameters correlate with survival: an analysis of the randomized phase 3 clinical trials in men with castration-resistant prostate cancer", Cancer Immunol. Immunother., 2013, vol. 62(1): 137-147.
Sims, R., "Development of sipuleucel-T: autologous cellular immunotherapy for the treatment of metastatic castrate resistant prostate cancer", Vaccine, 2012, vol. 30(29): 4394-4397.
Spisek, et al., "Maturation of dendritic cells by bacterial immunomodulators", Vaccine, 2004, vol. 22(21-22): 2761-2768.
Spisek, et al. "Phase I/II clinical trials of dendritic cell-based immotherapy in patients with the biochemical relapse of the prostate cancer", 2013 ASCO Annual Meeting, [Internet], Jun. 2013 [retrieved on Feb. 27, 2015], Retrieved from the Internet <URL: http://meetinglibrary.asco.org/content/116902-132>.
Svensson, et al., "Monocyte enriched apheresis for preparation of dendritic cells (DC) to be used in cellular therapy", Transfus. Apher. Sci., 2005, vol. 33(2): 165-173.
Take, et al., "Caspase activation in high-pressure-induced apoptosis of murine erythroleukemia cells", Jpn. J. Physiol., 2001, vol. 51(2): 193-199.
Tesniere, et al., "Molecular characteristics of immunogenic cancer cell death", Cell Death Differ., 2008, vol. 15(1): 3-12.
Thumann, et al., "Antigen loading of dendritic cells with whole tumor cell preparations", J. Immunol. Methods, 2003, vol. 277(1-2): 1-16.
Truxova, et al., "Day 3 Poly (I:C)-activated dendritic cells generated in CellGro for use in cancer immunotherapy trials are fully comparable to standard Day 5 DCs", Immunol. Lett., 2014, vol. 160(1): 39-49.

(56) References Cited

OTHER PUBLICATIONS

Truxova, et al. "High hydrostatic pressure to induce immunogenic cell death in human tumor cells", 2013 ASCO Annual Meeting, [Internet], Jun. 2013 [retrieved on Feb. 27, 2015], Retrieved from the Internet <URL: http://meetinglibrary.asco.org/content/116816-132>.
Vacchelli, et al., "Trial watch: Dendritic cell-based interventions for cancer therapy", Oncoimmunol., 2013, vol. 2(10): e25771 (1-15).
Vacchelli, et al., "Trial watch: Chemotherapy with immunogenic cell death inducers", Oncoimmunol., 2013, vol. 2(3): e23510 (1-11).
Weiss, et al., "Ex vivo- and in vivo-induced dead tumor cells as modulators of antitumor responses", Ann. NY Acad. Sci., 2010, vol. 1209(1):109-117.
Weiss, et al., "High hydrostatic pressure treatment generates inactivated mammalian tumor cells with immunogeneic features", J. Immunotoxicol., 2010, vol. 7(3): 194-204.
Zitvogel, et al., "Cancer despite immunosurveillance: immunoselection and immunosubversion", Nat. Rev. Immunol., 2006, vol. 6(10): 715-727.
Zitvogel, et al., "Immunological aspects of cancer chemotherapy", Nat. Rev. Immunol., 2008, vol. 8(1): 59-73.
Shen Li-qin et. al., "The Dendritic Cells Loaded with Autologous Tumor Antigen in Treatment.." Chinese Journal of Geriatrics, Sep. 2011, vol. 30 No. 9, p. 1-8.
L Potze et. al., "Betulinic acid-induced mitochondria-dependent cell death is counterbalanced by an autophagic salvage response," Cell Death and Disease (2014) vol. 5, p. 1-8.

* cited by examiner

A

D

CRYOPRESERVATION OF APOPTOTIC CANCER CELLS FOR USE IN IMMUNOTHERAPY AGAINST CANCER

1. FIELD

Described herein is a method for generating pharmaceutical compositions for use in immunotherapy. In specific embodiments, methods for cryopreserving cancer cells undergoing immunogenic cell death are provided for use in generating pharmaceutical compositions that can be used to activate dendritic cells for immunotherapy.

2. BACKGROUND

2.1 Dendritic Cell Immunotherapy

There is great interest in developing effective autologous immunotherapeutic vaccines for treating or preventing human cancer. Success at such autologous immunotherapy requires the development of a vaccine that is both specific for the patient's cancer and capable of eliciting a potent immune response.

Autologous dendritic cell therapy is an approach that involves priming a patient's immune system to attack the patient's cancer cells. In this procedure, certain immune cells, namely dendritic cells (DCs), are exposed to, or "pulsed" with, cancer cells comprising the patient's specific cancer antigens. The dendritic cells pulsed with specific cancer antigens then present these antigens to naïve T lymphocytes of the immune system. This leads to the priming of the T lymphocytes into a population of effector T lymphocytes, which attack cancer cells in the patient's body presenting those antigens.

To produce an autologous dendritic cell cancer vaccine, monocytes are collected from a cancer patient by leukapheresis. The monocytes are then differentiated in vitro into DCs, which are then pulsed with cancer cells related to the type of cancer being treated, and re-administrated to the patient to elicit an immune response against its cancer.

2.2 Cell Death

Cell death can be broadly classified into two types: necrosis and apoptosis. Necrosis is cell death caused by external factors damaging cells or tissue, whereas apoptosis is a programmed cell death which occurs naturally in living organisms. Cell death through either necrosis or apoptosis can be immunogenic or non-immunogenic. A specific type of apoptosis, characterized as immunogenic cell death (ICD), has been identified as being capable of inducing a robust immunogenic response. (G. Kroemer et al., 2013, Immunogenic Cell Death in Cancer therapy. Ann. Rev. Immunol., vol 31, pp. 51-72). Cells undergoing ICD are preferentially recognized by DCs, and can be used to pulse DCs, which, in turn, expose antigen from these dying cells to the immune system.

Despite the recent advances in the field of immunotherapy, the challenge of standardizing a process for producing an autologous cancer vaccine while ensuring optimal and reproducible antigen presentation by DCs after pulsing with cancer cells remains unmet.

3. SUMMARY

In one aspect, provided herein are methods and compositions for generating highly potent and immunogenic vaccines. In one embodiment, described herein is a method for producing a population of animal cells useful for immunotherapy, comprising: (a) inducing ICD in a population of animal cells expressing an antigen(s) of interest; (b) cryopreserving the cells undergoing ICD; and (c) thawing the cryopreserved cells. In another embodiment, described herein is a method for producing antigen-pulsed dendritic cells, comprising (a) inducing immunogenic cell death (ICD) in a population of animal cells expressing an antigen(s) of interest; (b) cryopreserving the cells undergoing ICD; (c) thawing the cells; and (d) pulsing dendritic cells with the thawed cells. In certain embodiments, the cells are expanded in cell culture prior to the induction of ICD. In specific embodiments, the animal cells express a cancer antigen(s) of interest. In some embodiments, the animal cells are cells derived from a subject having a disease. In a specific embodiment, the animal cells are from a cell line. In certain embodiments, the animal cells are from one, two, three or more cell lines. In a specific embodiment, the animal cells are human cells.

In another embodiment, described herein is a method for preparing a pharmaceutical composition for use in immunotherapy, comprising: (a) inducing ICD in a population of animal cells expressing an antigen(s) of interest; (b) cryopreserving the cells undergoing ICD; (c) thawing the cryopreserved cells; and (d) preparing a pharmaceutical composition comprising the thawed cells for use in immunotherapy. In certain embodiments, the cells are expanded in cell culture prior to the induction of ICD. In another embodiment, described herein is a method for producing a composition for immunotherapy, comprising: (a) expanding cells from an animal cell line expressing antigens of interest; (b) inducing the cells to undergo ICD; (c) cryopreserving the expanded cells undergoing ICD; (d) thawing the cryopreserved cells and (e) pulsing a population of dendritic cells with the thawed cells. In specific embodiments, the animal cells express cancer antigens of interest. In some embodiments, the animal cells are cells derived from a subject having a disease. In a specific embodiment, the animal cells are from a cell line. In certain embodiments, the animal cells are from one, two, three or more cell lines. In a specific embodiment, the animal cells are human cells.

In another embodiment, provided herein is a batch of vials comprising cryopreserved animal cells expressing an antigen(s) of interest. In specific embodiments, the animal cells express cancer antigens of interest. In a specific embodiment, the animal cells are from a cell line. In some embodiments, the animal cells are cells derived from a subject having a disease. In certain embodiments, the animal cells are from one, two, three or more cell lines. In a specific embodiment, the animal cells are human cells. In a specific embodiment, the batch of vials was produced by a method comprising: (a) inducing the cells to undergo ICD; and (b) cryopreserving the cells. In certain embodiments, the method further comprises expanding the cells prior to inducing the cells to undergo ICD. In some embodiments, a batch of vials is 3, 4, 5, 6, 7, 8, 9, 10, 11, 12, 13, 14, 15, 16, 17 or more vials.

In certain embodiments of the methods and compositions described herein, a single cell line is utilized. In other embodiments of the methods and compositions described herein, a combination of multiple (e.g., 2, 3, 4, 5, 6 or more) cell lines is utilized. In a specific embodiment, the cell line or cell line(s) selected for use in the methods and compositions described herein is based on the antigens expressed by the cell line or cell lines. In some embodiments, the cell line or cell lines selected for use in the methods and compositions described herein is according to the different sub-types of cancer or other disease (e.g., infectious disease) to be treated with immunotherapy. In certain embodiments, the cell line or cell lines selected for use in the methods and compositions is based on the antigens expressed by the cell line or cell lines and the sub-type of the cancer or other disease (e.g., infectious disease) to be treated with immunotherapy.

In a specific aspect, provided herein are methods and compositions for generating highly potent and immunogenic cancer vaccines specific to a patient's tumor. This aspect is based, in part, on the discovery and demonstration that cryopreservation of cancer cells in the critical stage of immunogenic cell death (ICD) is capable of producing a potent and highly effective vaccine against human cancer.

Because cancer cell undergoing ICD can ensure an optimal maturation of dendritic cells (DCs), activation of DCs by the dying cancer cells, and antigen presentation, cryopreservation of cancer cells at the stage of undergoing ICD has many advantages over alternative methods of producing and maintaining cancer cells and cell lines, including: (1) the ability to produce a standardized reagent that may be used to generate sufficient cancer vaccine for a series of immunotherapeutic treatments for multiple patients; (2) yielding a product that can be fully characterized and quality-control tested before its use in a manufacturing process; (3) eliminating the possibility of phenotypic drift in the tumor cell culture due to genetic instability or selective pressure; (4) eliminating the cost required to maintain cell cultures; and (5) decreasing the risk of exposure to microbes and to cross-contamination. Thus, the process of cryopreserving large amounts of tumor cell lines at a highly immunogenic stage of cell death not only standardizes the manufacturing process, but produces a potent autologous cancer vaccine capable of eliciting a vigorous and specific immune response in the cancer patient.

The use of cell lines to prepare the cancer vaccine provides the possibility of producing a large amount of cancer cells expressing the same cancer antigens, which, upon induction of ICD, can be cryopreserved in the form of ready-to-use aliquots of dying cancerous cells. After cryopreservation, each aliquot of the batch of cancer cells, upon thawing, retains the same physiological status, phenotype and genotype, immunogenicity and function properties as every other aliquot of the batch. Thus, the cryopreservation of dying cells undergoing ICD allows for standardization of the process, because DCs from any patient can be pulsed with a phenotypically and genotypically identical cancer cell population, expressing the same antigens in the same amounts, in which cell death was induced at the same time and in the same way. Such standardization allows for quality control and optimization of the preparation of cancer vaccines based on activated DCs.

In one embodiment, described herein is a method for producing a population of cancer cells useful for immunotherapy, comprising: (a) inducing ICD in a population of cancer cells; (b) cryopreserving the cancer cells undergoing ICD; and (c) thawing the cryopreserved cancer cells. In another embodiment, described herein is a method for producing antigen-pulsed dendritic cells, comprising (a) inducing immunogenic cell death (ICD) in a population of cancer cells; (b) cryopreserving the cancer cells undergoing ICD; (c) thawing the cancer cells; and (d) pulsing dendritic cells with the thawed cancer cells. In certain embodiments, the cancer cells are expanded in cell culture prior to the induction of ICD. In some embodiments, the cancer cells are cells derived from a subject having cancer. In a specific embodiment, the cancer cells are from a cancer cell line. In certain embodiments, the cancer cells are from one, two, three or more cancer cell lines. In a specific embodiment, the cancer cells are human cancer cells.

In another embodiment, described herein is a method for preparing a pharmaceutical composition for use in immunotherapy, comprising: (a) inducing ICD in a population of cancer cells; (b) cryopreserving the cancer cells undergoing ICD; (c) thawing the cryopreserved cancer cells; and (d) preparing a pharmaceutical composition comprising the thawed cancer cells for use in immunotherapy. In certain embodiments, the cancer cells are expanded in cell culture prior to the induction of ICD. In another embodiment, described herein is a method for producing a composition for immunotherapy, comprising: (a) expanding cancer cells; (b) inducing the cancer cells to undergo ICD; (c) cryopreserving the expanded cancer cells undergoing ICD; (d) thawing the cryopreserved cancer cells and (d) pulsing a population of dendritic cells with the thawed cancer cells. In some embodiments, the cancer cells are cells derived from a subject having cancer. In a specific embodiment, the cancer cells are from a cell line. In certain embodiments, the cancer cells are from one, two, three or more cancer cell lines. In a specific embodiment, the cancer cells are human cancer cells.

In another embodiment, provided herein is a batch of vials comprising cryopreserved cancer cells. In a specific embodiment, the cancer cells are from a cancer cell line. In some embodiments, the cancer cells are cells derived from a subject having cancer. In certain embodiments, the cancer cells are from one, two, three or more cancer cell lines. In a specific embodiment, the cancer cells are human cancer cells. In a specific embodiment, the batch of vials was produced by a method comprising: (a) inducing the cancer cells to undergo ICD; and (b) cryopreserving the cancer cells. In certain embodiments, the method further comprises expanding the cancer cells prior to inducing the cells to undergo ICD. In some embodiments, a batch of vials is 3, 4, 5, 6, 7, 8, 9, 10, 11, 12, 13, 14, 15, 16, 17 or more vials.

In another embodiment, described herein is a vial comprising a population cancer cells, wherein the population of cancer cells are a cryopreserved population of cancer cells undergoing immunogenic cell death.

In certain embodiments of the methods and compositions described herein, the cancer cell line is prostate cancer cell line, ovarian cancer cell line, or lung cancer cell line. In some embodiments of the methods and compositions described herein, the cancer cell lines is a glioblastoma cell line, renal cancer cell line, colon cancer cell line, or breast cancer cell line.

In certain embodiments of the methods and compositions described herein, a single cancer cell line is utilized. In other embodiments of the methods and compositions described herein, a combination of multiple (e.g., 2, 3, 4, 5, 6 or more) cancer cell lines is utilized. In a specific embodiment, the cancer cell line or cancer cell line(s) selected for use in the methods and compositions described herein is based on the antigens expressed by the cancer cell line or cancer cell lines. In some embodiments, the cell line or cell lines selected for use in the methods and compositions described herein is according to the different sub-types of cancer to be treated with immunotherapy. In certain embodiments, the cancer cell line or cancer cell lines selected for use in the methods and compositions is based on the antigens expressed by the cancer cell line or cancer cell lines and the sub-type of the cancer to be treated with immunotherapy.

In another embodiment of the methods and compositions, population of cancer cells used to pulse a population of dendritic cells is a cancerous cell line. In another embodiment, a plurality of cancer cell lines related to a same type of cancer is combined. In a specific embodiment, the cancer is a solid tumor cancer. In certain embodiments, the solid tumor cancer is prostate cancer, ovarian cancer, lung cancer, renal cancer, colon cancer, breast cancer or glioblastoma.

In one embodiment, the cancer to be treated by immunotherapy is prostate cancer and the cancerous cell line to be used to activate DCs is the LNCap cell line. In another embodiment, the cancer to be treated by immunotherapy is ovarian cancer and two cancerous cell lines are used to activate DCs, namely the cell line SK-OV-3 and the cell line OV-90. In yet another embodiment, the cancer to be treated by immunotherapy is lung cancer and two cells lines are used to activate DCs, namely NCI-H520 and NCI-H522 cells lines.

In a specific embodiment, any pharmacological or mechanical inducer of ICD can be used to induce immunogenic cell death of the cells to be cryopreserved. Identified inducers of ICD include: anthracyclines, anti-EGFR antibodies, Big Potassium channel antagonists, bortezomib, cardiac glycosides, cyclophosphamide, GADD43/PP1 inhibitors and mitomycin, irradiation by UV light or gamma rays, oxaliplatin, photodynamic therapy with hypericin, poly (I:C), thapsigargin and cisplatin, high hydrostatic pressure. In certain embodiments of the methods described herein, ICD is induced by high hydrostatic pressure, anthracyclines, anti-EGFR antibodies, Big Potassium channel antagonists, bortezomib, cardiac glycosides, cyclophosphamide, GADD43/PP1 inhibitors and mitomycin, irradiation by UV light or gamma rays, oxaliplatin, photodynamic therapy with hypericin, poly(I:C), thapsigargin and cisplatin, or any other agent inducing immunogenic cell death. In a preferred embodiment, high hydrostatic pressure is used to induce ICD. In another embodiment, UV is used to induce ICD. In another embodiment, anthracyclines are used to induce ICD. In another embodiment, photodynamic therapy with hypericin is used to induce ICD. The regimen and type of pharmacological inducers of ICD might change from one cell (e.g., one cancerous cell) to another to obtain an optimal a maturation and activation of DCs.

In certain embodiments of the methods and compositions described herein, the animal cells (e.g., cancer cells) undergoing immunogenic cell death are preserved in a cryopreservant solution. In a specific embodiment of the methods and compositions described herein, animal cells (e.g., cancer cells) undergoing immunogenic cell death are preserved in a cryopreservant solution containing at least 5% of dimethyl sulfoxide. In another embodiment of the methods and compositions described herein, animal cells (e.g., cancer cells) undergoing immunogenic cell death are preserved in a cryopreservant solution containing at least 5% of glycerol.

In another embodiment of the methods and compositions described herein, cells undergoing ICD are kept frozen at temperatures below −75° C. In a specific embodiment of the methods and compositions described herein, cells undergoing ICD are kept frozen at temperatures of at least or below −130° C. In another embodiment, dying cells in cryopreservant are cooled at a rate of −1 to −5° C./min. In another embodiment of the methods and compositions described herein, dying cells are exposed to temperatures of −25 to −30° C. for up to 30 min before transferring to lower temperatures such as −130° C.

In another of the methods and compositions described herein, the aliquots of dying cells are transferred to a heavily insulated box and placed at −80° C. for 24 hours and then transferred to lower temperatures such as −130° C. In another embodiment of the methods and compositions described herein, the aliquots of dying cells are transferred to cooling boxes containing 100% isopropyl alcohol for 24 hours, allowing freezing at a rate close to −1° C./min when place at −80° C. The aliquots can then be transferred to lower temperatures such as −130° C.

In another embodiment, the dying cells are cryopreserved immediately after induction of cell death by pharmacological or mechanical agents. In another embodiment of the methods and compositions described herein the dying cells are kept into culture for up to six hours after the induction of immunogenic cell death prior to cryopreservation.

In another embodiment of the methods and compositions described herein, the thawed cells undergoing ICD are put back into culture in culture media for at least one hour and not more than six hours before being incubated with DCs.

In an embodiment of the methods and compositions described herein, the hallmarks of immunogenic cell death are preserved during cryopreservation. In another specific embodiment of the methods and compositions described herein, after thawing, the cells undergoing cell death retain the hallmarks of immunogenic cell death. In another embodiment of the methods and compositions described herein, the type of cell death before and after freezing is the same type of cell death.

In another aspect, provided herein is a pharmaceutical pack or kit comprising one or more containers comprising cryopreserved cells undergoing ICD. The pharmaceutical pack or kit may include instructions for use of the cryopreserved cells described herein.

4. DESCRIPTION OF THE DRAWINGS

FIGS. 1A, 1B, 1C, 1D, and 1E. Cryopreservation of HHP-treated tumor cells preserves the apoptotic character of cell death and the expression of immunogenic cell death markers. (A) The prostate cell line (LNCap) and ovarian cell line (SKOV3) were treated by HHP and cryopreserved after time 0 and 4H. After thawing process in the time points 0H and 4H, the apoptosis level as the percentage of early (annexin V+/DAPI−) and late (annexinV+/DAPI+) apoptotic cells was determined by flow cytometry. (B) Dot plots of the representative experiments are shown. Cells were labeled with DAPI and annexin V-Alexa 647. (C) The kinetics of HSP70, HSP90 and calreticulin surface expression by the prostate LNCap cell line and SKOV3 cell line following treatment with 250 MPa for 10 min and cryopreservation and thawing process. The expression of the indicated markers by treated cells is shown as the mean fluorescence intensity (MFI). The compiled results of a total of 3 experiments are shown. *, P<0.05. (D) Stability of expression of IMM during the long time course of 3 months for prostate (LNCap) and ovarian (SKOV3) cell line. (E) Confocal microscopy images of HHP-treated cells, cryopreserved and thawed in different time points.

Figure 2A:
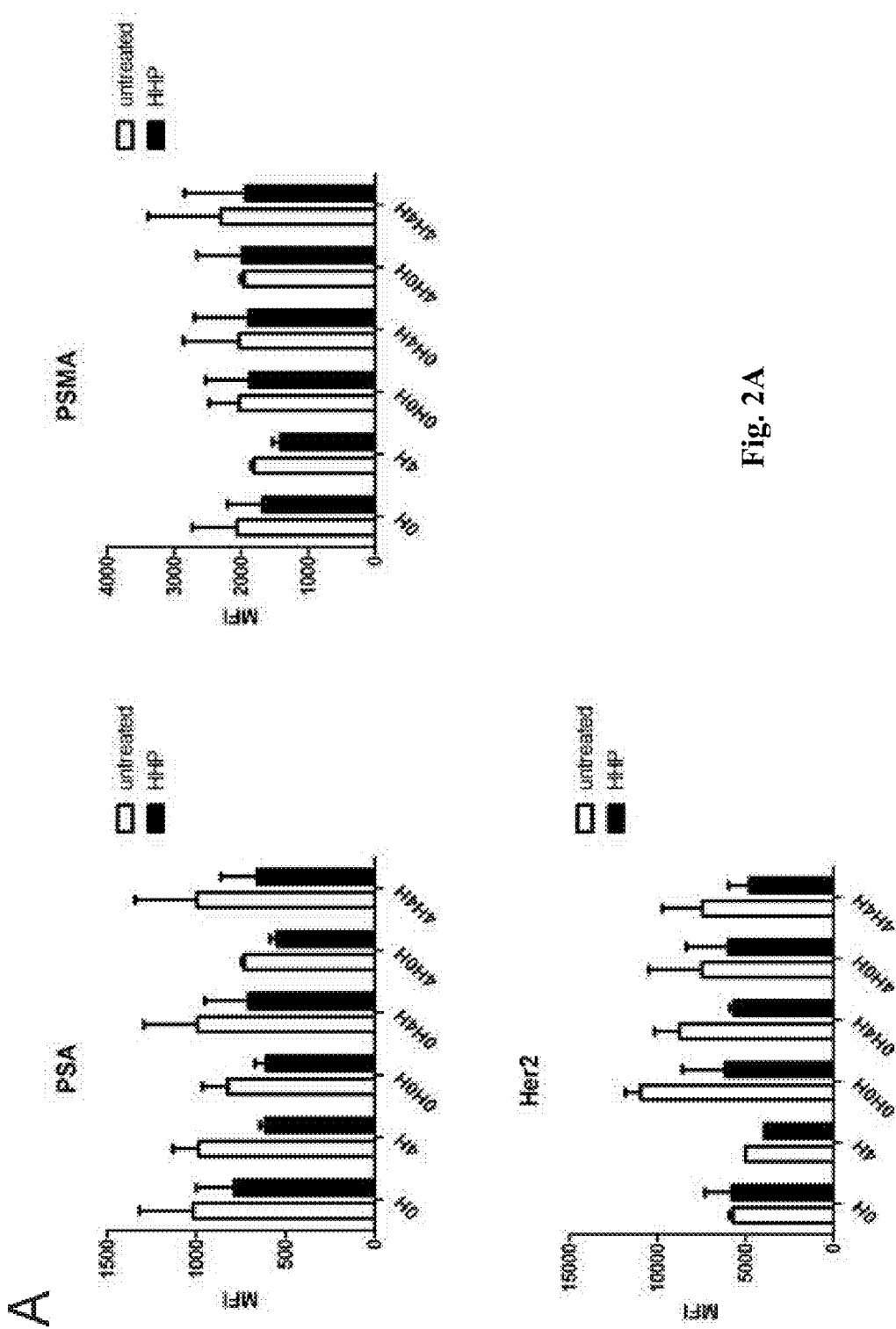
Figure 2B:
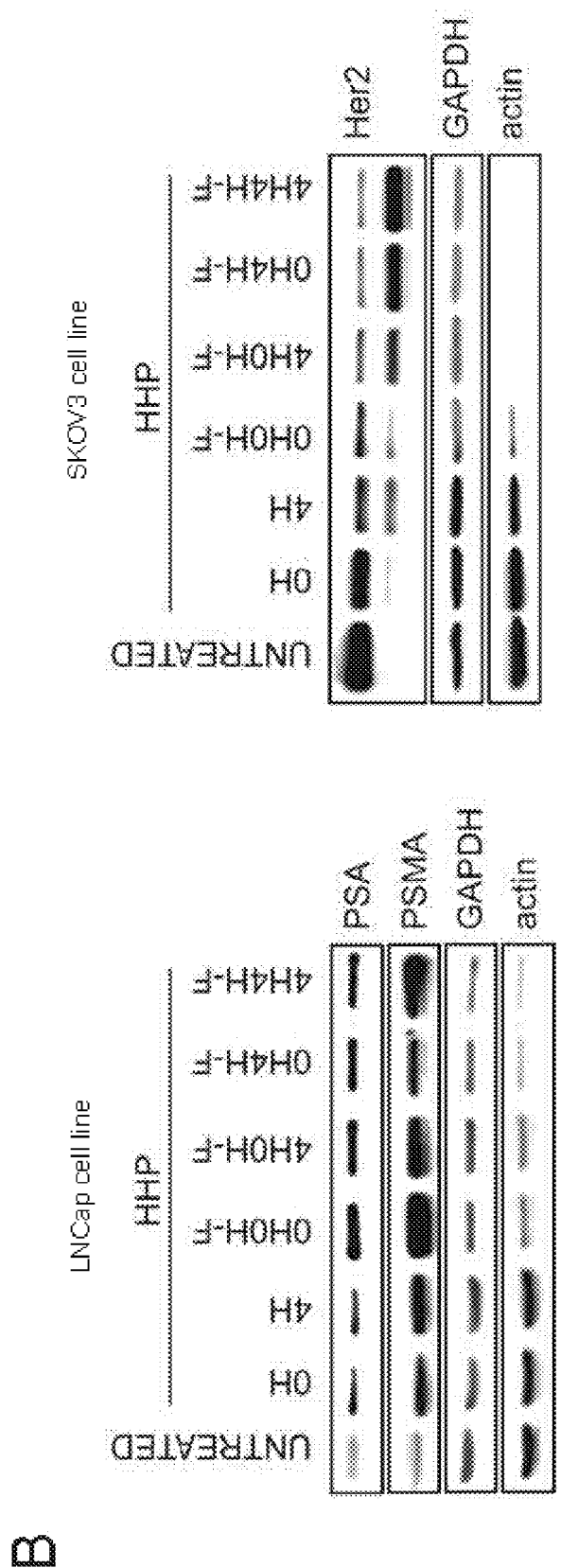

FIGS. 2A and 2B. HHP treatment and cryopreservation of tumor cells induce positively an accumulation of tumor antigens compared to other cytoskeletal proteins. (A) Expression of PSA and PSMA tumor antigens on the cell surface of prostate LNCap cancer cells and the expression of Her2/Neu tumor antigen on the cell surface of SKOV3 cancer cell line after HHP treatment and cryopreservation and thawing process in different time points by flow cytometry. The MFI values of 3 independent experiments are shown. *, P<0.05 as compared to untreated tumor cells. (B)

The whole cell amount of PSA, PSMA and Her2/Neu proteins in HHP-treated cryopreserved cells by western blot analysis. The data show the compiled results (mean±SD) of 3 independent experiments. *, P<0.05 as compared to untreated tumor cells.

Figures 3A, 3B:
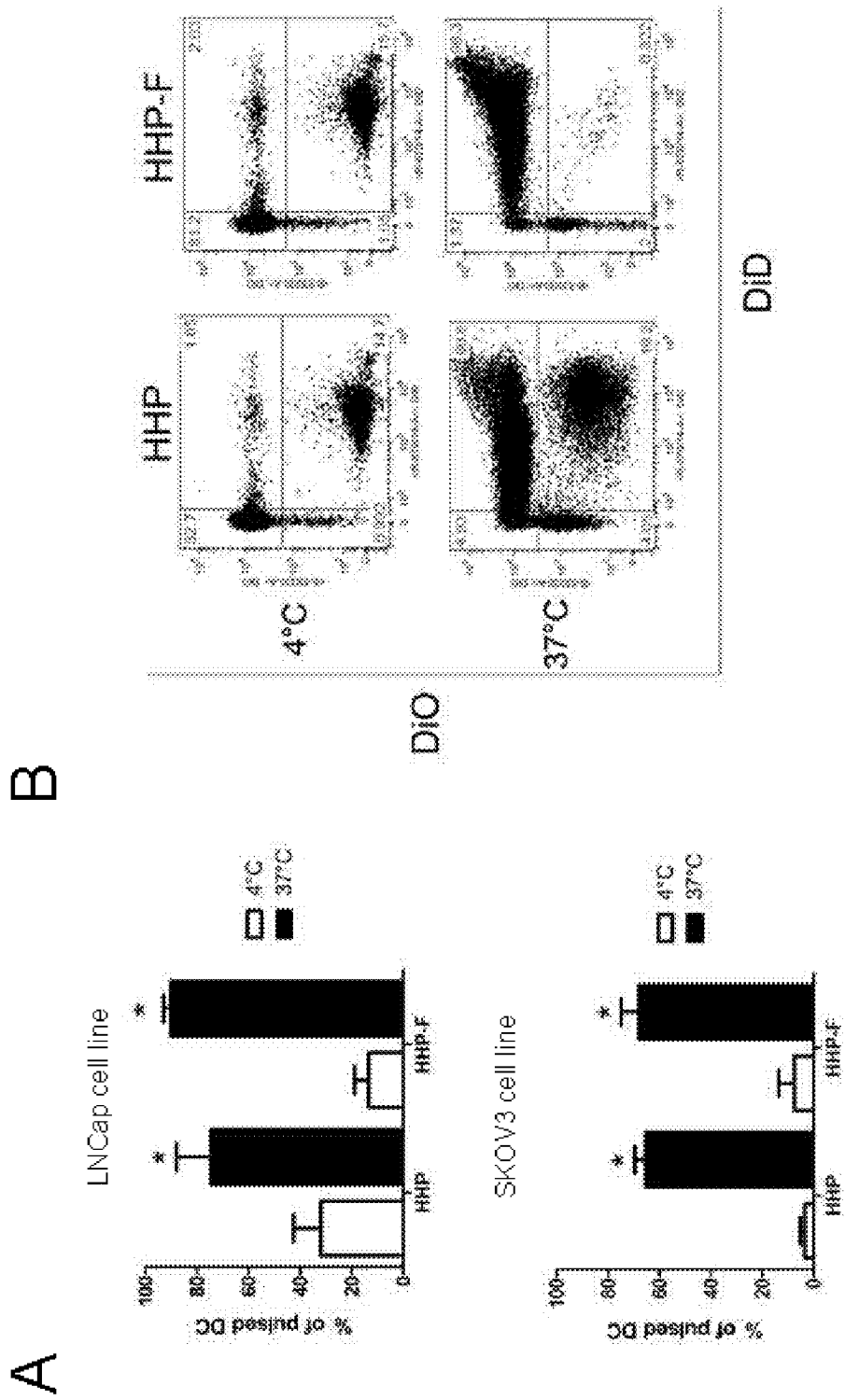
Figure 3C:
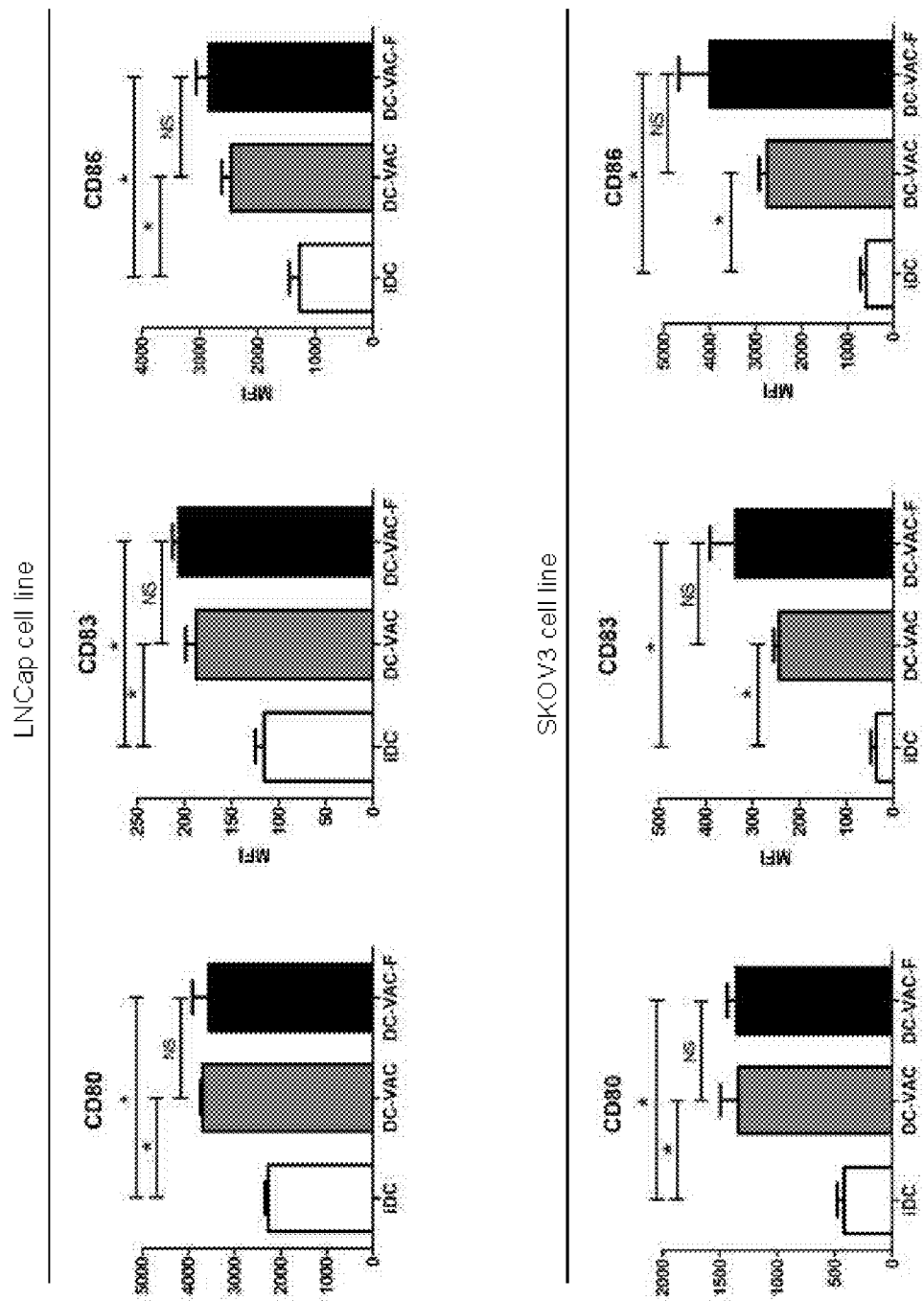

FIGS. 3A, 3B, and 3C. HHP-frozen tumor cells are phagocytosed by DCs at the same level as non-frozen cells. (A) Killed LNCap and SKOV3 cell lines were labeled with DiO and cocultured with DiD-labeled immature DCs. Percentage of phagocytosis at 24 h following HHP treatment and cryopreservation as compared to control. (B) Dot plots of representative experiments are shown. (C) Immature DCs (day 5) were cultured for 24 h with LNCap cells and SKOV3 cells treated by HHP and cryopreserved. After 24 h, the expression of CD80, CD83, CD86 and CCR7 by DCs was analyzed by flow cytometry. The MFI values are shown of 3 independent experiments. *, P<0.05. as compared to untreated tumor cells.

Figure 4A:
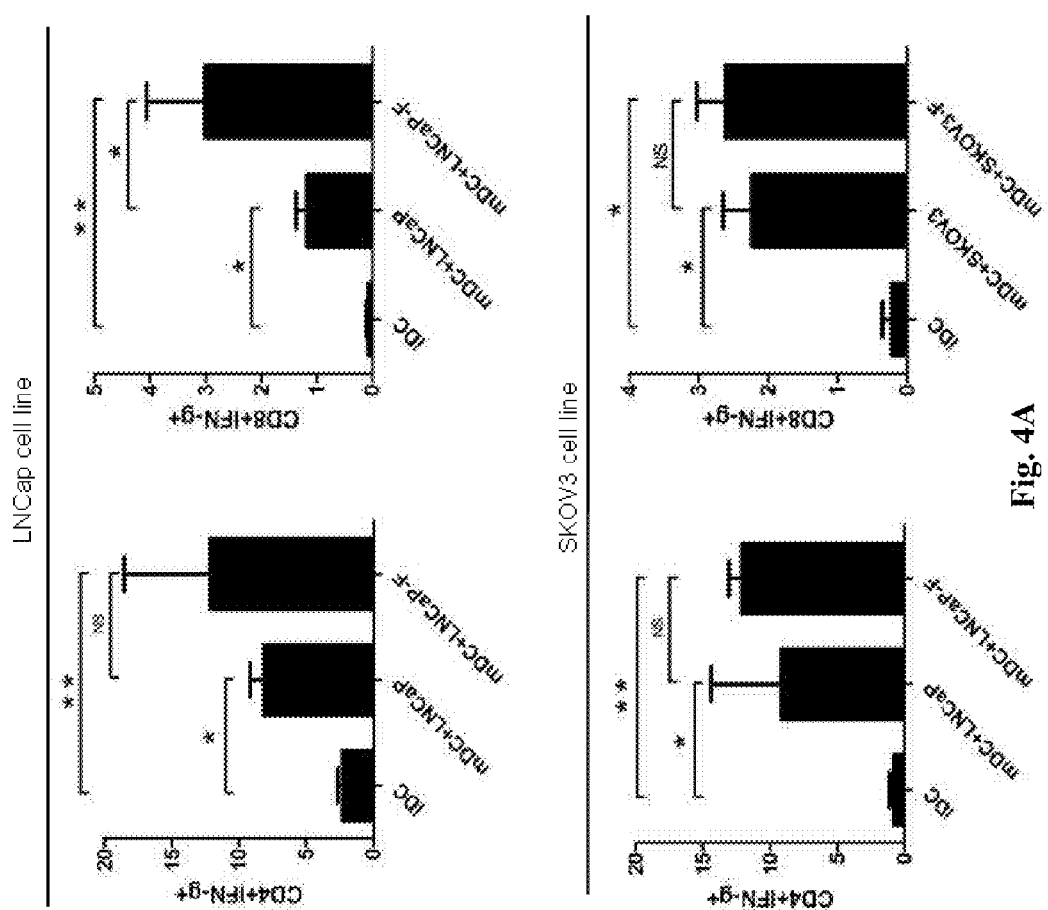
Figure 4B:
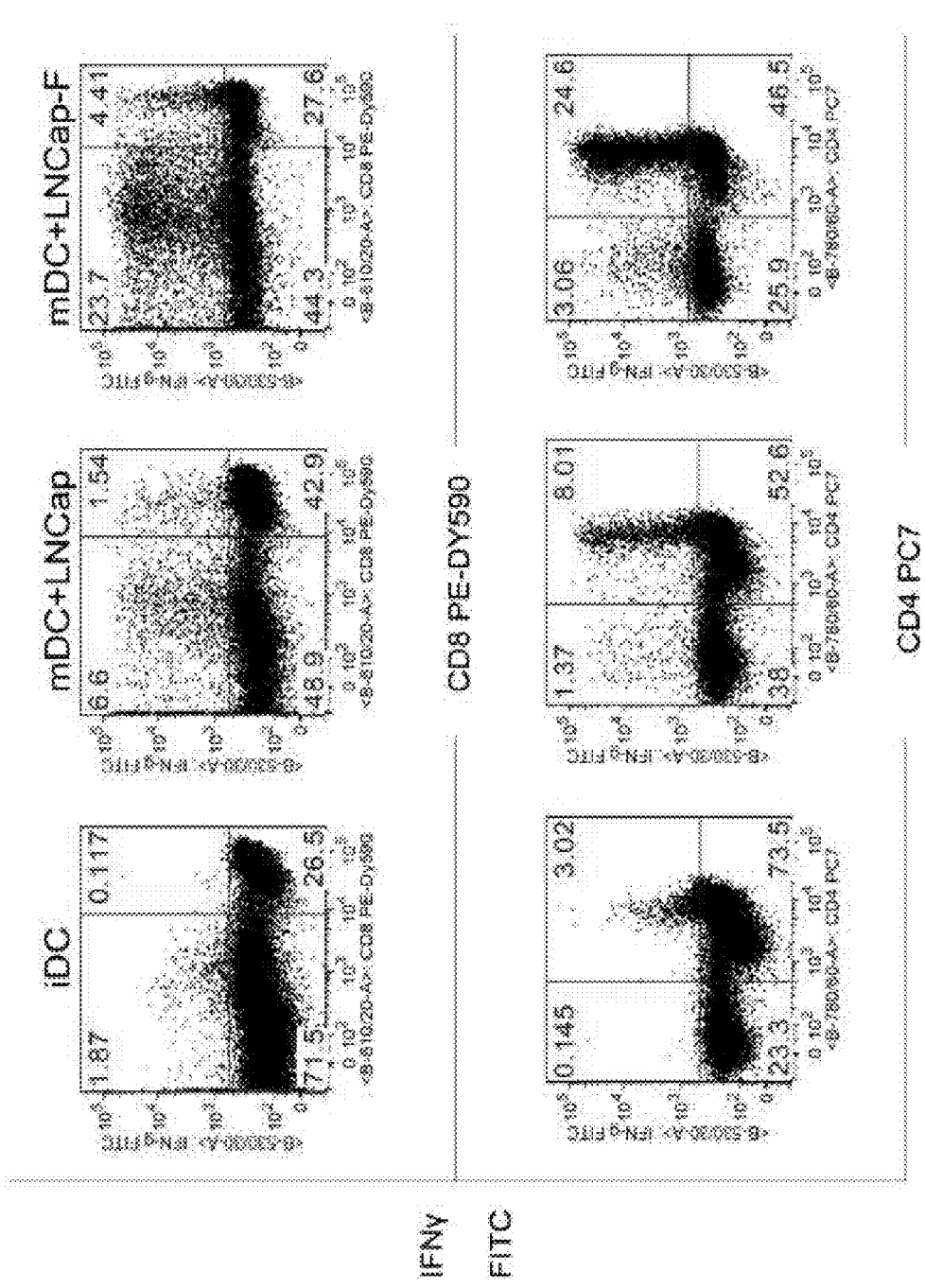

FIGS. 4A and 4B. DCs pulsed with HHP-frozen tumor cells induce tumor-specific T cells. (A) Monocyte-derived DCs were pulsed with LNCap or SKOV3 cells killed by HHP and cryopreserved and then used to stimulate autologous T cells for 2 weeks. The number of IFN-γ-producing cells in cultures with unpulsed DCs or DCs pulsed with tumor cells non-frozen and frozen was analyzed by intracellular IFN-γ staining after restimulation. The data show a summary and (B) representative staining of 3 independent experiments. *, P<0.05 as compared to untreated tumor cells.

5. DETAILED DESCRIPTION

5.1 Terminology

In describing and claiming the invention, the following terms should be understood as follows.

The term "isolated cell" or "isolated population of cells" means any cell or population of cells of any organism that does not naturally occur in nature. The term "isolated host cell" means any cell of any organism that is removed from its natural environment and selected, modified, transformed, grown, used or manipulated in any way, for the production of a substance by the cell, for example the expression by the cell of a gene, a DNA or RNA sequence, a protein or an enzyme. Isolated cells, population of cells, host cells, and genetically engineered cells include isolated immune cells or a population of immune cells, such as monocytes and dendritic cells.

To "expand," "specifically expand" or "preferentially expand" in the context of dendritic cells means to culture a population of monocytes in a media containing growth factor inducing the proliferation and differentiation of the monocytes into immature dendritic cells. In a preferred embodiment, monocytes are expended and differentiated into DCs with GM-CSF and IL4.

An "autologous cell" refers to a cell which was derived from the same individual that is being treated by cell therapy.

A "donor cell" refers to a cell that was derived from an individual other than the individual being treated by cell therapy.

An "allogeneic cell" refers to a genetically distinct cell.

As used herein, the terms "treat," "treating," and "treatment" in the context of the administration of a therapy to a subject refer to the beneficial effects that a subject derives from a therapy. In certain embodiments, treatment of a subject with a cancer vaccine described herein achieves at least one, two, three, four or more of the following effects: (i) the reduction or amelioration of the severity of one or more symptoms of cancer; (ii) the reduction in the duration of one or more symptoms associated with cancer; (iii) the protection against the recurrence of a symptom associated with cancer; (iv) the reduction in hospitalization of a subject; (v) a reduction in hospitalization length; (vi) the increase in the survival of a subject; (vii) the enhancement or improvement of the therapeutic effect of another therapy; (viii) an increase in the survival rate of patients; (xiii) a decrease in hospitalization rate; (ix) the protection against the development or onset of one or more symptoms associated with cancer; (x) the reduction in the number of symptoms associated with cancer; (xi) an increase in symptom-free survival of cancer patients; (xii) improvement in quality of life as assessed by methods well known in the art; (xiii) the protection against the recurrence of a tumor; (xiv) the regression of tumors and/or one or more symptoms associated therewith; (xvii) the inhibition of the progression of tumors and/or one or more symptoms associated therewith; (xviii) a reduction in the growth of a tumor; (xix) a decrease in tumor size (e.g., volume or diameter); (xx) a reduction in the formation of a newly formed tumor; (xxi) eradication, removal, or control of primary, regional and/or metastatic tumors; (xxii) a decrease in the number or size of metastases; (xxiii) a reduction in mortality; (xxiv) an increase in the tumor-free survival rate of patients; (xxv) an increase in relapse free survival; (xxvi) an increase in the number of patients in remission; (xxvii) the size of the tumor is maintained and does not increase or increases by less than the increase of a tumor after administration of a standard therapy as measured by conventional methods available to one of skill in the art, such as magnetic resonance imaging (MRI), dynamic contrast-enhanced MRI (DCE-MRI), X-ray, and computed tomography (CT) scan, or a positron emission tomography (PET) scan; r (xxviii) an increase in the length of remission in patients; and/or (xxiv) a decrease in measurable cancer antigens As used herein, term "protecting against" in the context of administering a therapy to a subject refers to the prophylactic effect that a subject receives from a therapy. In a specific embodiment, this term refers to the inhibition of the development or onset of cancer or a symptom associated therewith, or inhibition of the recurrence of cancer or a symptom thereof.

As used herein, the terms "manage," "managing," and "management," in the context of the administration of a therapy to a subject, refer to the beneficial effects that a subject derives from a therapy, which does not result in a cure of a disease. In certain embodiments, a subject is administered one or more therapies to "manage" cancer so as to prevent the progression or worsening of symptoms associated with the cancer.

As used herein, the terms "subject" and "patient" are used interchangeably and refer to an animal. In a specific embodiment, such terms refer to a mammal such as a non-primate (e.g., cows, pigs, horses, cats, dogs, rats etc.) and a primate (e.g., monkey and human), most preferably a human.

As used herein, the term "significant," as in "significant" amount, change or effect, for example, means that the amount, change, or effect produced would not be likely to have occurred by random chance, as determined by any standard method for statistical analysis, such as a p test, wherein a p value less than the critical alpha level indicates that an event would be unlikely. Thus, a "significant" change in the context of this invention indicates the p value is less than the critical alpha level, and that the probability is small that the change happened by chance.

As used herein, the term "effective amount" in the context of the administration of a therapy to a subject refers to the amount of a therapy that achieves a desired prophylactic or therapeutic effect. Examples of effective amounts are provided in Section 5.9.2, infra.

As used herein "not significantly altered" means a change in that a amount or effect produced would is not statistically significant, as determined by any standard method for statistical analysis, such as a p test. In a specific embodiment, the p value is 0.5, 0.1, 0.05, 0.001, 0.005, or 0.0001.

All terms used herein, unless otherwise defined, will be given their ordinary technical or scientific meaning as would be commonly understood by one of ordinary skill in the art at the time of the disclosure.

5.2 Methods for Inducing Immunogenic Cell Death

In one aspect, provided are methods for inducing a specific type of apoptotsis characterized as immunogenic cell death ("ICD") in animal cells expressing an antigen(s) of interest. In a specific aspect, provided are methods for inducing a specific type of apoptotsis characterized as immunogenic cell death ("ICD") in cancer cells. ICD is the only type of cell death which is capable of producing a robust immune response against antigens expressed by dying cells. The hallmarks of ICD are the expression of immunogenic molecules on the cell surface such as HSP70, HSP90 and calreticulin and the release of late apoptotic markers HMGB1 and ATP. The interaction of DCs with a cell, such as a cancer cell, dying under ICD conditions leads to a more rapid rate of DC phagocytosis and significant maturation of DCs. DCs treated with ICD dying cancer cells induce high numbers of tumor-specific T lymphocytes.

Any technique known in the art may be used to induce ICD of animal cells expressing an antigen(s) of interest (e.g., cancer cells). As a person skilled in the art will appreciate, not all techniques known to induce apoptosis will necessarily induce ICD. Only apoptotic agents inducing ICD will elicit the most efficient DC maturation.

In one embodiment, a pharmacological agent(s) is used to induce ICD. In another embodiment, a mechanical technique(s) is used to induce ICD. In another embodiment, a combination of a pharmacological agent(s) and a mechanical technique(s) is used to induce ICD. The regimen and type of pharmacological inducer(s) and/or mechanical inducer(s) of ICD might vary depending on the cancerous cells. The pharmacological inducers and/or mechanical inducers of ICD used to obtain an optimal maturation and activation of DCs may differ from one type of cancer cell to another type of cancer cell.

Examples of inducers of ICD include, but are not limited to, anthracyclines, anti-EGFR antibodies, Big Potassium channel antagonists, bortezomib, cardiac glycosides, cyclophosphamide, GADD43/PP1 inhibitors and mitomycin, irradiation by UV light or gamma rays, oxaliplatin, photodynamic therapy with hypericin, poly (I:C), thapsigargin and cisplatin, and high hydrostatic pressure. In a specific embodiment, high hydrostatic pressure ("HHP") is used to induced ICD. See, e.g., International Publication No. WO 2013/004708 A1 for a discussion of ICD induced by HHP. In another embodiment, UV light is used to induce ICD. In another embodiment, anthracyclines are used to induce ICD. In another embodiment, photodynamic therapy with hypericin is used to induce ICD.

The hallmarks of ICD are the expression of immunogenic molecules on the cell surface, such as HSP70, HSP90 and calreticulin, and the release of late apoptotic markers HMGB1 and ATP. Techniques known to one skilled in the art can be used to assess the expression of these cell surface markers and the release of the late apoptotic makers. For example, the expression of the cell surface markers can be assessed using standard techniques such as flow cytometry, immunocytochemistry (e.g., staining with tissue specific or cell-marker specific antibodies), fluorescence activated cell sorting (FACS), and magnetic activated cell sorting (MACS). Fluorescence activated cell sorting (FACS) is a well-known method for separating particles, including cells, based on the fluorescent properties of the particles (Kamarch, 1987, Methods Enzymol, 151:150-165). Laser excitation of fluorescent moieties in the individual particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used. FACS sorted particles may be directly deposited into individual wells of 96-well or 384-well plates to facilitate separation and cloning. The release of the HMGB1 can be assessed by, e.g., enzyme-linked immunosorbent assay-based methodologies (ELISA), western blot, or other similar methods known in the art.

Apoptosis can be quantitated by measuring DNA fragmentation. Commercial photometric methods for the quantitative in vitro determination of DNA fragmentation are available. Examples of such assays, including TUNEL (which detects incorporation of labeled nucleotides in fragmented DNA) and ELISA-based assays, are described in Biochemica, 1999, no. 2, pp. 34 37 (Roche Molecular Biochemicals). Apoptosis can also be observed morphologically. Apoptosis can also be assessed by annexin V fluorescein staining, such as described in Section 6, infra.

In a specific embodiment, one or more of the assays described in Section 6, infra, can be utilized to assess the induction of ICD.

In specific embodiments, the cancer cells induced to undergo ICD may be cryopreserved immediately, or a few minutes (e.g., 10 minutes, 15 minutes, 30 minutes, or 45 hours) or a few hours (e.g., within 1 hour, 1.5 hours, 2 hours, 2.5 hours, 3 hours, 3.5 hours, 4 hours, 4.5 hours, 5 hours, 5.5 hours, 6 hours, 6.5 hours, 7 hours, 7.5 hours, or 8 hours) after induction of ICD. In one embodiment, cancer cells induced to undergo ICD are kept in cell culture for at least one hour and not more than six hours before being cryopreserved. In a specific embodiment, cancer cells induced to undergo ICD kept in cell culture for 0.5 hours to 1 hour, 1 hour to 2 hours, 1.5 hours to 2 hours, 1.5 hours to 2.5 hours, 2 hours to 3 hours, 2 to 4 hours, 3 hours to 4 hours, 4 hours to 5 hours, 3 hours to 6 hours, 4 hours to 6 hours, 5 hours to 6 hours, 2 to 4 hours, 2 to 5 hours, 3 to 5 hours, 2 hours to 6 hours, or 3 hours to 6 hours before being cryopreserved. In another specific embodiment, cancer cells induced to undergo ICD kept in cell culture for 1.5 hours, 2 hours, 2.5 hours, 3 hours, 3.5 hours, 4 hours, 4.5 hours, 5 hours, 5.5 hours or 6 hours before being cryopreserved.

In a certain embodiments, the cancer cells induced to undergo ICD are characterized prior to cryopreservation using techniques described herein (e.g., in this Section 5 or Section 6, infra) or known to one skilled in the art for characterizing cells undergoing ICD. In a specific embodiment, at least 50%, at least 55%, at least 60%, at least 65%, at least 70%, at least 75%, at least 80%, at least 85%, at least 90%, at least 95%, at least 98% of the cancer cells induced to undergo ICD are characterized as undergoing ICD using techniques described herein or known to one skilled in the art before cryopreservation. In another embodiment, 50% to 75%, 50% to 99%, 75% to 85%, 75% to 90%, 75% to 99%, 80% to 90%, 80% to 99%, 85% to 90%, 85% to 95%, or 95% to 99% of the cancer cells induced to undergo ICD are characterized as undergoing ICD using techniques described herein or known to one skilled in the art before cryopreservation.

In another specific embodiment, at least 50%, at least 55%, at least 60%, at least 65%, at least 70%, at least 75%, at least 80%, at least 85%, at least 90%, at least 95%, at least 98% of the cancer cells induced to undergo ICD are characterized as undergoing ICD by the expression of one or more ICD markers, such as HSP70, HSP90, or calreticulin, using techniques described herein or known to one skilled in the art before cryopreservation. In another embodiment, 50% to 75%, 50% to 99%, 75% to 85%, 75% to 90%, 75% to 99%, 80% to 90%, 80% to 99%, 85% to 90%, 85% to 95%, or 95% to 99% of the cancer cells induced to undergo ICD are characterized as undergoing ICD by the expression of one or more ICD markers, such as HSP70, HSP90, or calreticulin, using techniques described herein or known to one skilled in the art before cryopreservation.

5.3 Type of Cancer Cells Induced to Undergo Immunogenic Cell Death

In one aspect, the cancer cells induced to undergo ICD are from a cancer cell line. The type of cancer cell line can be chosen accordingly to the type of cancer to be treated in the patient or to the type of antigens expressed by the cancer cell line. Multiple cancer cell lines related to a same type of cancer can be combined to assure a broad spectrum of expressed antigens and a more efficient cancer vaccine.

In a specific embodiment, the cancer cells induced to undergo ICD are from a solid tumor. In certain embodiments, the cancer cells induced to undergo ICD are mesothelioma cells, melanoma cells, adenoma cells, carcinoma cells, adenocarcinoma cells, ductal carcinoma cells, rhabdomyosarcoma cells, osteosarcoma cells, neuroblastoma cells, astrocytoma cells, or glioblastoma cells. In one embodiment, the cancer cells induced to undergo ICD are from a carcinoma, such as an adenocarcinoma, an adrenocortical carcinoma, a colon adenocarcinoma, a colorectal adenocarcinoma, a colorectal carcinoma, a ductal cell carcinoma, a lung carcinoma, a thyroid carcinoma, a hepatocellular carcinoma, a nasopharyngeal carcinoma, or an unspecified carcinoma. In another embodiment, the cancer cells induced to undergo ICD are from a melanoma (e.g., a malignant melanoma), a non-melanoma skin carcinoma. In another embodiment, the cancer cells induced to undergo cell deathICD are from a desmoid tumor, a desmoplastic small round cell tumor; an endocrine tumor, an Ewing sarcoma, a germ cell tumor (e.g., testicular cancer, ovarian cancer, choriocarcinoma, endodermal sinus tumor, germinoma, etc.), a hepatosblastoma, a neuroblastoma; a non-rhabdomyosarcoma soft tissue sarcoma; an osteosarcoma, a retinoblastoma, a rhabdomyosarcoma, or a Wilms tumor. In another embodiment, the cancer cells induced to undergo ICD are from an acoustic neuroma; an astrocytoma (e.g., a grade I pilocytic astrocytoma, a grade II low-grade astrocytoma, a grade III anaplastic astrocytoma, or a grade IV glioblastoma multiforme); a chordoma; a craniopharyngioma; a glioma (e.g., a brain stem glioma; an ependymoma; a mixed glioma; an optic nerve glioma; or a sub-ependymoma); a glioblastoma; a medulloblastoma; a meningioma; a metastatic brain tumor; an oligodendroglioma; a pineoblastoma; a pituitary tumor; a primitive neuroectodermal tumor; or a schwannoma. In another embodiment, the cancer cells induced to undergo ICD are from pancreatic cancer, breast cancer, brain cancer, renal cancer, prostate, cervical cancer, liver cancer, colorectal cancer, ovarian cancer, colon cancer, testicular cancer, thyroid cancer, lung cancer, or breast cancer. In a certain embodiments, the cancer cells induced to undergo ICD are from a malignant tumor. In a specific aspect, in accordance with the embodiments in this paragraph, the cancer cells from these types of cancers/tumors are cell lines.

In another embodiment, the cancer cells induced to undergo ICD are from a benign tumor. In another embodiment, the cancer cells induced to undergo ICD are from a solid tumor cancer comprising prostate cancer, ovarian cancer, lung cancer, renal cancer, colon cancer, breast cancer or glioblastoma. In a specific aspect, in accordance with the embodiments in this paragraph, the cancer cells from these types of cancers/tumors are cell lines.

In some embodiments, the cancer cells induced to undergo ICD are leukemia cells, acute myelogenous leukemia cells, acute myeloid leukemia cells, acute T cell leukemia cells, acute lymphoblastic leukemia cells, hairy cell leukemia cells, acute promyelocytic leukemia cells, lymphoma cells, Burkitt's lymphoma cells, B cell chronic lymphocytic leukemia cells, non-Hodgkin's lymphoma cells, Hodgkin's lymphoma cells, or multiple myeloma cells. In certain embodiments, the cancer cells induced to undergo ICD are tumor stem cells or cancer stem cells. In a specific aspect, in accordance with the embodiments in this paragraph, the cancer cells from these types of cancers are cell lines.

In certain embodiments, the cancer cells induced to undergo ICD are cancer cell line cells. Examples of cancer cell lines include, but are not limited to, 5637 (Carcinoma), KHOS/NP (Osteosarcoma), MNNG/HOS (Osteosarcoma), Saos-2 (Osteosarcoma), U-2 OS (Osteosarcoma), SJSA-1 (Osteosarcoma), CCF-STTG1 (Astrocytoma), DBTRG-05MG (Glioblastoma), U87 MG (Glioblastoma), T98G (Glioblastoma), SK-N-SH (Neuroblastoma), SK-N-AS (Neuroblastoma), MCF-7 (Adenocarcinoma), MDA-MB-231 (Adenocarcinoma), MDA-MB-436 (Adenocarcinoma), SK-BR-3 (Adenocarcinoma), BT-20 (Carcinoma), BT-474 (Carcinoma), CAMA-1 (Carcinoma), HCC2218 (Carcinoma), SW527 (Carcinoma), MDA-MB-453 (Carcinoma), MDA-MB-4355 (Carcinoma), T-47D (Carcinoma), ZR-75-1 (Carcinoma), UACC-812 (Carcinoma), HCC1419 (Carcinoma), HeLa (Adenocarcinoma), Caco-2 (Adenocarcinoma), COL0205 (Adenocarcinoma), COL0320/DM (Adenocarcinoma), DLD-1 (Adenocarcinoma), HCT-15 (Adenocarcinoma), SK-CO-1 (Adenocarcinoma), SW48 (Adenocarcinoma), SW480 (Adenocarcinoma), HCT-8 (Adenocarcinoma), RKO (Carcinoma), LS411N (Carcinoma), T84 (Carcinoma), AGS (Adenocarcinoma), KATO III (Carcinoma), NCI-N87 (Carcinoma), SNU-16 (Carcinoma), 769-P (Adenocarcinoma), 786-O (Adenocarcinoma), ACHN (Adenocarcinoma), A-498 (Carcinoma), Caki-1 (Carcinoma), G-402 (Leiomyoblastoma), CML-T1 (Leukemia), CTV-1 (Leukemia), JVM-2 (Leukemia), K562 (Leukemia), MHH-CALL2 (Leukemia), NALM-6 (Leukemia), 8E5 (Leukemia), CCRF-SB (Leukemia), CEM/C1 (Leukemia), CEM/C2 (Leukemia), CEM-CM3 (Leukemia), CCRF-HSB-2 (Leukemia), KG-1 (Leukemia), KG-la (Leukemia), CCRF-CEM (Leukemia), MOLT-3 (Leukemia), SUP-B15

(Leukemia), TALL-104 (Leukemia), Loucy (Leukemia), RS4; 11 (Leukemia), REH (Leukemia), AML-193 (Leukemia), THP-1 (Leukemia), MOLM-13 (Leukemia), Kasumi-1 (Leukemia), Kasumi-3 (Leukemia), BDCM (Leukemia), HL-60 (Leukemia), I 2.1 (Leukemia), I 9.2 (Leukemia), J.gamma1.WT (Leukemia), J.RT3-T3.5 (Leukemia), P116 (Leukemia), P116.c139 [P116.c39] (Leukemia), D1.1 (Leukemia), J45.01 (Leukemia), MV-4-11 (Leukemia), Kasumi-4 (Leukemia), MEG-01 (Leukemia), KU812 (Leukemia), Mo (Leukemia), JM1 (Leukemia), GDM-1 (Leukemia), CESS (Leukemia), ARH-77 (Leukemia), SK-HEP-1 (Adenocarcinoma), Bel-7402 (Carcinoma), Bel-7404 (Carcinoma), HEP-3B (Carcinoma), HepG2 (Carcinoma), Calu-3 (Adenocarcinoma), NCI-H1395 (Adenocarcinoma), NCI-H1975 (Adenocarcinoma), SK-LU-1 (Adenocarcinoma), NCI-H2122 (Adenocarcinoma), NCI-H727 (Carcinoid), A-427 (Carcinoma), A549 (Carcinoma), SW1573 (Carcinoma), NCI-H358 (Carcinoma), NCI-H460 (Carcinoma), NCI-H292 (Carcinoma), NCI-H82 (Carcinoma), NCI-H226 (Carcinoma), NCI-H526 (Carcinoma), or MSTO-211H (Mesothelioma). In certain embodiments, the cancer cells induced to undergo ICD are from the ovarian cell line SK-OV3 or OV-90. In some embodiments, the cancer cells induced to undergo ICD are from the lung cancer cell line NCI-H520 or NCI-H522. In certain embodiments, the cancer cells induced to undergo ICD are from the prostate cancer cell line LNCap.

In certain embodiments, the cancer cells induced to undergo ICD are from a single cancer cell line. In other embodiments, the cancer cells induced to undergo ICD are from a combination of two, three, four, five or more cancer cell lines. For example, the cancer cells induced to undergo ICD may be from the SK-OV3 and OV-90 cell lines. In another example, the cancer cells induced to undergo ICD may be from the NCI-H520 and NCI-H522 cell lines. In specific embodiments, the cancer cells induced to undergo ICD are from a combination of cancer cell lines from the same type of cancer. For example, the cancer cells induced to undergo ICD may be from two, three, four, five or more lung cancer cell lines. In another example, the cancer cells induced to undergo ICD may be from two, three, four, five or more prostate cancer cell lines. In certain embodiments, the cancer cells induced to undergo ICD are chosen based upon the cancer antigens the cells express.

In some embodiments, the cancer cells induced to undergo ICD are obtained from a patient's tumor. Techniques known to one of skill in the art may be used to obtain cancer cells from a patient's tumor. In some embodiments, a biopsy of a patient's tumor is obtained. The biopsy can be from any organ or tissue, for example, skin, liver, lung, heart, colon, kidney, bone marrow, teeth, lymph node, hair, spleen, brain, breast, or other organs. Any biopsy technique known by those skilled in the art can be used for isolating a tumor sample from a patient, for instance, open biopsy, close biopsy, core biopsy, incisional biopsy, excisional biopsy, or fine needle aspiration biopsy. In certain embodiments, the tumor biopsy is stored before the cancer cells are isolated. The tumor biopsy may be stored for 30 minutes, 60 minutes, 1 hour, 2 hours, 3 hours, 4 hours, 6 hours, 12 hours, 18 hours, 24 hours 48 hours, 72 hours, 1 week, two weeks, three weeks, 1 month, 2 months or more before cancer cells are isolated and induced to undergo ICD. In certain embodiments, cancer cells isolated from a tumor biopsy are stored for a period of time before they are induced to undergo ICD. The cancer cells may be stored for 15 minutes, 30 minutes, 60 minutes, 1 hour, 2 hours, 3 hours, 4 hours, 6 hours, 12 hours, 18 hours, 24 hours 48 hours, 72 hours, 1 week, two weeks, three weeks, 1 month, 2 months or more before they are induced to undergo ICD. In some embodiments, cancer cells obtained from a tumor biopsy are immediately induced to undergo ICD. In a specific embodiment, cancer cells obtained from a patient's tumor are utilized to create a cancer cell line and the cancer cell line is induced to undergo ICD.

5.4 Methods for Cryopreserving Cells Induced to Undergo Immunogenic Cell Death In one aspect, described herein is the use of cryopreservation, the long-term storage of biological materials at very low temperature, to maintain a reproducible source of cancer cells undergoing ICD for extended periods of time. In a specific aspect, the cancer cells are in the process of dying under ICD conditions prior to cryopreservation. Cells prepared in this way retain the ICD conditions after cryopreservation when thawed.

Methods for cryopreservation of cells are well known in the art. See, e.g., C. B. Morris, "Cryopreservaton of Animal and Human Cell Lines" (2007), in Methods in Molecular Biology, vol 368: Cryopreservation and Freeze-Drying Protocols, 2nd Ed. (J. G. Day and G. N. Stacey eds.), Humana Press Inc. Totowa, N.J., pp. 227-236, which is incorporated herein in its entirety.

In one aspect, cryopreservant solutions are used to hold the cancer cells in a fixed state of ICD for extended periods of time. The same cryopreservants used to maintain cells alive may be used to maintain dying cells is their specific ICD conditions during and after cryopreservation.

Any cryoperservant available in the art may be used. In a specific embodiment, cancer cells undergoing ICD are preserved in a cryopreservant solution containing at least 5% of dimethyl sulfoxide. In certain embodiments, cancer cells undergoing ICD are preserved in a cryopreservant solution containing 5%, 6%, 7%, 8%, 9%, 10%, 11%, 12%, 13%, 14%, 15%, 16%, 17%, 18%, 19% or 20% dimethyl sulfoxide. In some embodiments, cancer cells undergoing ICD are preserved in a cryopreservant solution containing 5% to 10%, 10% to 15% or 15% to 20% dimethyl sulfoxide. In another embodiment, cancer cells undergoing ICD are preserved in a cryopreservant solution containing at least 5% of glycerol. In certain embodiments, cancer cells undergoing ICD are preserved in a cryopreservant solution containing 5%, 6%, 7%, 8%, 9%, 10%, 11%, 12%, 13%, 14%, 15%, 16%, 17%, 18%, 19% or 20% of glycerol. In some embodiments, cancer cells undergoing ICD are preserved in a cryopreservant solution containing 5% to 10%, 10% to 15% or 15% to 20% glycerol.

Cryoperservants are commercially available; in one preferred embodiment a cryoperservant having 10% DMSO is used, such as the commercially available CryoStor CS10.

In one embodiment, to retain the cancer cells in the best conditions during cryopreservation, cancer cells are cooled at a constant slow rate. In one embodiment, cancer cells undergoing ICD in cryopreservant are cooled at a rate of −1 to −5° C./min, or −2 to −5° C./min, −3 to −5° C./min, −4 to −5° C./min, −5 to −6° C./min, −5 to −7° C./min, −5 to −8° C./min, −5 to −9° C./min, −5 to −10° C./min, −7 to −10° C./min, or −8 to −10° C./min. In another embodiment, cancer cells undergoing ICD in cryopreservant are cooled at a rate of −1° C./min, −2° C./min, −3° C./min, −4° C./min, −5° C./min, −6° C./min, −7° C./min, −8° C./min, −9° C./min or −10° C./min. In another embodiment, cancer cells undergoing ICD are exposed to temperatures of −25 to −30° C. or −30 to −35° C. for up to 30 min before transferring to lower temperatures such as −130° C. In another embodiment, cancer cells undergoing ICD are exposed to temperatures of −24° C., −25° C., −26° C., −27° C., −28° C., −29° C., −30° C., −31° C., −32° C., −33° C., −34° C. or −35° C. to −30° C. for 1 to 45 minutes (e.g., 1 minute, 2 minutes, 3 minutes, 4 minutes, 5 minutes, 10 minutes, 15 minutes, 20 minutes, 25 minutes, 30 minutes, 35 minutes, 40 minutes or 45 minutes) before transferring to lower temperatures such as −120° C., −125° C., −130° C., −135° C., or −140° C.

In one embodiment, to insure optimal cryopreservation, cancer cells in cryopreservants are frozen and kept at very low temperatures. In one embodiment, cancer cells undergoing ICD are kept frozen at temperatures below −75° C. (e.g., −80° C., −85° C., −90° C., −95° C., −100° C., −105° C., −110° C., −115° C., −120° C., −125° C. or −130° C.). In a specific embodiment, cells undergoing ICD are kept frozen at temperatures of at least or below −130° C. (e.g., −135° C., −140° C., −145° C., −150° C., −155° C., −160° C., −165° C., −170° C., −175° C., or −180° C.).

In another embodiment, aliquots of cancer cells undergoing ICD are transferred to a heavily insulated box and placed at −80° C. for 24 hours and then transferred to lower temperatures such as −130° C., −135° C., −140° C., −145° C., −150° C., −155° C., −160° C., −165° C., −170° C., −175° C., or −180° C. In another embodiment, aliquots of cancer cells undergoing ICD are transferred to cooling boxes containing 100% isopropyl alcohol for 24 hours, allowing freezing at a rate close to −1° C./min when place at −80° C. The aliquots are then transferred to lower temperatures such as −130° C., −135° C., −140° C., −145° C., −150° C., −155° C., −160° C., −165° C., −170° C., −175° C., or −180° C.

In a specific embodiment, cells undergoing ICD are cryopreserved as described in Section 6, infra.

In a specific embodiment, aliquots of cancer cells undergoing ICD are cryopreserved as described herein. For examples, cancer cells undergoing ICD may be aliquoted into 1, 2, 3, 4, 5, 6, 7, 8, 9, 10, 11, 12, 13, 14, 15, 16, 17, 18, 19, 20 or more containers, such as vials, and then cryopreserved as described herein. In another specific embodiment, cancer cells induced to undergo ICD may be cryopreserved in cryopreservant solution as described herein and aliquoted in 1, 2, 3, 4, 5, 6, 7, 8, 9, 10, 11, 12, 13, 14, 15, 16, 17, 18, 19, 20 or more containers, such as vials. In certain embodiments, a container (e.g., a vial) of cryopreserved cancer cells contains 100, 150, 200, 250, 300, 350, 400, 450, 500, 550, 600, 650, 700, 750, 800, 850, 900, 950 or 1000 cancer cells induced to undergo ICD. In some embodiments, a container (e.g., a vial) of cryopreserved cancer cells contains $1\times10^2$, $5\times10^2$, $1\times10^3$, $5\times10^3$, $1\times10^4$, $5\times10^4$, $1\times10^5$, $5\times10^5$, $1\times10^6$, $5\times10^6$, $1\times10^7$, $5\times10^7$ or $1\times10^8$ cancer cells induced to undergo ICD. In certain embodiments, a container (e.g., a vial) of cryopreserved cancer cells contains $1\times10^1$ to $1\times10^2$, $1\times10^2$ to $5\times10^2$, $1\times10^2$ to $1\times10^3$, $1\times10^3$ to $5\times10^3$, $1\times10^2$ to $1\times10^4$, $1\times10^3$ to $5\times10^4$, $1\times10^3$ to $1\times10^4$, $1\times10^2$ to $1\times10^5$, $1\times10^2$ to $5\times10^5$, $1\times10^2$ to $1\times10^6$, $1\times10^3$ to $5\times10^6$, $1\times10^4$ to $1\times10^7$, $1\times10^5$ to $1\times10^7$, $1\times10^5$ to $1\times10^7$, $1\times10^6$ to $1\times10^8$, $1\times10^7$ to $1\times10^8$ cancer cells induced to undergo ICD.

In some embodiments, a batch of cancer cells are induced to undergo ICD, aliquots of the cancer cells are cryopreserved in separate containers (e.g., 1 to 25, 25 to 50, 50 to 75, 75 to 100, 100 to 125, 125 to 150, 150 to 200 or more containers, such as vials), and 1, 2 or 3 more of the vials may be thawed each time dendritic cells need to be pulsed with cancer cells to produce a cancer vaccine. In certain embodiments, a container (e.g, a vial) of cryopreserved cancer cells contains 100, 150, 200, 250, 300, 350, 400, 450, 500, 550, 600, 650, 700, 750, 800, 850, 900, 950 or 1000 cancer cells induced to undergo ICD. In some embodiments, a container (e.g., a vial) of cryopreserved cancer cells contains $1\times10^2$, $5\times10^2$, $1\times10^3$, $5\times10^3$, $1\times10^4$, $5\times10^4$, $1\times10^5$, $5\times10^5$, $1\times10^6$, $5\times10^6$, $1\times10^7$, $5\times10^7$ or $1\times10^8$ cancer cells induced to undergo ICD. In certain embodiments, a container (e.g., a vial) of cryopreserved cancer cells contains $1\times10^1$ to $1\times10^2$, $1\times10^2$ to $5\times10^2$, $1\times10^2$ to $1\times10^3$, $1\times10^3$ to $5\times10^3$, $1\times10^2$ to $1\times10^4$, $1\times10^3$ to $5\times10^4$, $1\times10^3$ to $1\times10^4$, $1\times10^2$ to $1\times10^5$, $1\times10^2$ to $5\times10^5$, $1\times10^2$ to $1\times10^6$, $1\times10^3$ to $5\times10^6$, $1\times10^4$ to $1\times10^7$, $1\times10^5$ to $1\times10^7$, $1\times10^5$ to $1\times10^7$, $1\times10^6$ to $1\times10^8$, $1\times10^7$ to $1\times10^8$ cancer cells induced to undergo ICD.

5.5 Methods for Thawing Cryopreserved Cells

As for living cells, the way dying cells are recovered after cryopreservation is crucial to maintain the preferred type of cell death. In a preferred embodiment, cryopreserved cancer cells undergoing ICD are thawed rapidly, preferably between 10 seconds and 5 mins. In one embodiment, cryopreserved cells are thawed at a temperature of 32° C., 33° C., 34° C., 35° C., 36° C., 37° C., 38° C., 39° C. or 40° C. for between 5 secs. and 10 mins. In a specific embodiment, cells undergoing ICD are thawed by warming a container (e.g., a vial) of cryopreserved cells in the palms of the hand for between 10 secs. and 5 mins. In a specific embodiment, cryopreserved cancer cells undergoing ICD are thawed as described in Section 6, infra.

It is known that freezing and thawing, when non-optimal conditions are used, can induce cell death. Such cell death is typically necrosis, which is an undesired type of cell death for the maturation of DCs. It is therefore critical when freezing and thawing dying cells to ensure that ICD is maintained before and after cryopreservation.

In one embodiment, the cryopreserved cancer cells undergoing ICD are thawed and may be used immediately or a few hours after thawing for the incubation with DCs. In specific embodiments, the cells undergoing ICD may be used immediately, or a few minutes (e.g., 10 minutes, 15 minutes, 30 minutes, or 45 hours) or a few hours (e.g., within 1 hour, 1.5 hours, 2 hours, 2.5 hours, 3 hours, 3.5 hours, or 4 hours) after thawing for the incubation with DCs. In one embodiment, the thawed cells undergoing ICD are put back into culture in culture media for at least one hour and not more than six hours before being incubated with DCs. In a specific embodiment, the thawed cells undergoing ICD are put back into culture in culture media for 1.5 hours, 2 hours, 2.5 hours, 3 hours, 3.5 hours, 4 hours, 4.5 hours, 5 hours, 5.5 hours, 6 hours, 6.5 hours or 7 hours before being incubated with DCs. In another specific embodiment, the thawed cells undergoing ICD are put back into culture in culture media for 0.5 to 1 hour, 1 to 2 hours, 1.5 hours to 2 hours, 2 to 3 hours, 2 to 4 hours, 2.5 hours to 3 hours, 3 to 3.5 hours, 2 to 4 hours, 3 to 4 hours, 4 to 4.5 hours, 4 to 5 hours, 4 to 6 hours, 5 to 6 hours, 1 to 6 hours, 2 to 6 hours, or 5 to 7 hours before being incubated with DCs.

In a specific embodiment, cryopreserved cancer cells are thawed and characterized as undergoing ICD using techniques described herein (e.g., in Section 5.2, supra, or Section 6, infra) or known to one skilled the art. In another specific embodiment, the cryopreserved cancer cells induced to undergo ICD are stable as assessed by the expression of certain markers, such as ICD markers (e.g., HSP70, HSP90 and calreticulin). Techniques known to one skilled in the art, such as immunofluorescence, can be used to assess the expression of such markers. In a specific embodiment, the expression of ICD markers is assessed as described in Section 6, infra. In certain embodiments, greater than 50% of the cryopreserved cancer cells express ICD markers after thawing. In specific embodiments, approximately 55%, approximately 60%, approximately 65%, approximately 70%, approximately 75%, approximately 80%, approximately 85%, approximately 90%, approximately 95% or approximately 98% of the cryopreserved cancer cells express ICD markers after thawing. In some embodiments, approximately 55% to approximately 65%, approximately 65% to approximately 85%, or approximately 75%, to approximately 85%, approximately 80% to approximately 90% or approximately 90% to approximately 95% of the cryopreserved cancer cells express ICD markers after thawing. In a specific embodiment, the expression of ICD markers, such as HSP70, HSP90 and calreticulin, by cryopreserved cancer cells undergoing ICD after thawing is not significantly altered relative to non-cryopreserved/thawed cancer cells induced to undergo ICD.

In another embodiment, the expression of tumor antigens by cryopreserved cancer cells undergoing ICD after thawing is not significantly altered relative to non-cryopreserved/thawed cancer cells induced to undergo ICD. Techniques known to one skilled in the art, such as immunofluorescence, flow cytometry, and ELISA, can be used to assess the expression of tumor antigens. In a specific embodiment, the expression of tumor antigens is assessed as described in Section 6, infra.

In another embodiment, the ability of cryopreserved cancer cells undergoing ICD after thawing to be phagocytosed by dendritic cells is not significantly altered as compared to the phagocytosis of non-cryopreserved/thawed cancer cells induced to undergo ICD. Techniques known to one skilled in the art can be used to assess the phagocytosis of cancer cells undergoing ICD by dendritic cells. In a specific embodiment, the phagocytosis of cancer cells undergoing ICD by dendritic cells is assessed as described in Section 6, infra.

In another embodiment, the ability of cryopreserved cancer cells undergoing ICD after thawing to induce the maturation of dendritic cells is not significantly altered relative to the ability of non-cryopreserved/thawed cancer cells induced to undergo ICD to induce the maturation of dendritic cells. In a specific embodiment, the maturation of dendritic cells is assessed by the expression of cell markers, such as CD80, CD83 and CD86. Techniques known to one skilled in the art, such as flow cytometry and FACS, can be used to assess the expression of such cell markers. In a specific embodiment, the maturation of dendritic cells is assessed as described in Section 6, infra.

In a specific embodiment, dendritic cells pulsed with cryopreserved cancer cells undergoing ICD after thawing are capable of inducing tumor-specific T cells. In another specific embodiment, dendritic cells pulsed with cryopreserved cancer cells undergoing ICD after thawing induce tumor-specific T cells at levels not significantly different than dendritic cells pulsed with non-cryopreserved/thawed cancer cells induced to undergo ICD. Techniques known to one skilled in the art can be used to assess the induction of tumor-specific T cells. In a specific embodiment, the induction of tumor-specific T cells is assessed as described in Section 6, infra.

5.6 Methods for Generating Dendritic Cells

Techniques known to one skilled in the art may be used to obtain/generate dendritic cells from peripheral blood mononuclear cells or a bone marrow sample. In a specific embodiment, a whole blood sample is obtained from a patient and peripheral blood mononuclear cells are isolated. Mononuclear cells may be isolated from peripheral blood of a patient by, for example, Ficoll-Paque Plus gradient centrifugation. In addition, mononuclear cells can be fractionated using a fluorescence activated cell sorter (FACS) or magnetic activated cell sorting (MACS). Dendritic cells can be enriched by sequential density centrifugation of apheresis peripheral blood mononuclear cells. The monocytes isolated from the blood of a patient may be cultured in the presence of factors, such as GM-CSF and IL-4 or Flt3L, to differentiate into immature DCs after a period of, e.g., 4 to 5 days. To generate mature dendritic cells, the cells may be activated with TNF-α, IFN-γ, LPS, CpG, IL-1 or CD40L. In a specific embodiment, mature dendritic cells are activated using TLR-3 and/or TLR-4 activators, such as poly (I:C) and/or LPS. Further, CMRF-44 antigen, CD1c, BDCA-4 and other dendritic cell-specific markers may also be used to promote DC maturation. In a specific embodiment, dendritic cells are generated as described in Section 6, infra.

Techniques known to one skilled in the art can be used to assess/confirm the presence of dendritic cells. For example, the presence of dendritic cells can be assessed/confirmed detecting the expression of dendritic cell surface markers using techniques, such as FACS. In a specific embodiment, the presence of dendritic cells is assessed/confirmed using the methods in Section 6, infra.

5.7 Methods for Producing Cancer Vaccines

In certain embodiments, dendritic cells are pulsed with the cancer cells undergoing ICD and the pulsed dendritic cells are the cancer vaccine administered to a patient. In a preferred embodiment, the cancer cells undergoing ICD were cryopreserved and thawed before being used to pulse dendritic cells. In a specific embodiment, the pulsed dendritic cells are autologous to the patient receiving the cancer vaccine.

In some embodiments, dendritic cells are pulsed with the cancer cells undergoing ICD, the pulsed dendritic cells are co-cultured with lymphocytes (e.g., T lymphocytes) and the lymphocytes are administered to a patient as the cancer vaccine. In a specific embodiment, the pulsed dendritic cells and the lymphocytes are autologous to the patient receiving the cancer vaccine.

Techniques known to one skilled in the art can be used to pulse dendritic cells with cancer cells undergoing ICD. Further, techniques known to one skilled in the art can be used to co-culture lymphocytes with pulsed dendritic cells.

In a specific embodiment, dendritic cells are pulsed with the cancer cells undergoing ICD as described in Section 6, infra.

5.8 Methods for Treating Cancer Using Cancer Vaccines

In a specific aspect, presented herein are methods for treating, protecting against, and/or managing cancer, comprising administering to a subject in need thereof an effective amount of a cancer vaccine described herein or a composition thereof. In a specific embodiment, a cancer vaccine described herein or a composition thereof is the only active agent administered to a subject. In certain embodiments, the cancer vaccine described herein that is administered to the subject comprises autologous dendritic cells.

In specific embodiments, the administration of a cancer vaccine described herein or a composition thereof to a subject with cancer (in some embodiments, an animal model for cancer) achieves at least one, two, three, four or more of the following effects: (i) the reduction or amelioration of the severity of one or more symptoms of cancer; (ii) the reduction in the duration of one or more symptoms associated with cancer; (iii) the protection against the recurrence of a symptom associated with cancer; (iv) the reduction in hospitalization of a subject; (v) a reduction in hospitalization length; (vi) the increase in the survival of a subject; (vii) the enhancement or improvement of the therapeutic effect of another therapy; (viii) an increase in the survival rate of patients; (xiii) a decrease in hospitalization rate; (ix) the protection against the development or onset of one or more symptoms associated with cancer; (x) the reduction in the number of symptoms associated with cancer; (xi) an increase in symptom-free survival of cancer patients; (xii) improvement in quality of life as assessed by methods well known in the art; (xiii) the protection against the recurrence of a tumor; (xiv) the regression of tumors and/or one or more symptoms associated therewith; (xvii) the inhibition of the progression of tumors and/or one or more symptoms associated therewith; (xviii) a reduction in the growth of a tumor; (xix) a decrease in tumor size (e.g., volume or diameter); (xx) a reduction in the formation of a newly formed tumor; (xxi) eradication, removal, or control of primary, regional and/or metastatic tumors; (xxii) a decrease in the number or size of metastases; (xxiii) a reduction in mortality; (xxiv) an increase in the tumor-free survival rate of patients; (xxv) an increase in relapse free survival; (xxvi) an increase in the number of patients in remission; (xxvii) the size of the tumor is maintained and does not increase or increases by less than the increase of a tumor after administration of a standard therapy as measured by conventional methods available to one of skill in the art, such as magnetic resonance imaging (MRI), dynamic contrast-enhanced MRI (DCE-MRI), X-ray, and computed tomography (CT) scan, or a positron emission tomography (PET) scan; (xxviii) an increase in the length of remission in patients; and/or (xxiv) decrease in measurable cancer antigens.

In a specific embodiment, the administration of a cancer vaccine described herein or a composition thereof to a subject with cancer (in some embodiments, an animal model for cancer) inhibits or reduces the growth of a tumor by at least 2-fold, preferably at least 2.5-fold, at least 3-fold, at least 4-fold, at least 5-fold, at least 7-fold, or at least 10-fold relative to the growth of a tumor in a subject with cancer (in some embodiments, in the same animal model for cancer) administered a negative control as measured using assays well known in the art. In another embodiment, the administration of a cancer vaccine described herein or a composition comprising a cancer vaccine described herein to a subject with cancer (in some embodiments, an animal model for cancer) inhibits or reduces the growth of a tumor by at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% relative to the growth of a tumor in a subject with cancer (in some embodiments, in the same animal model for cancer) administered a negative control as measured using assays well known in the art.

In a specific embodiment, the administration of a cancer vaccine described herein or a composition comprising a cancer vaccine described herein to a subject with cancer (in some embodiments, an animal model for cancer) reduces the size of a tumor by at least 2-fold, preferably at least 2.5-fold, at least 3-fold, at least 4-fold, at least 5-fold, at least 7-fold, or at least 10-fold relative to the growth of a tumor in a subject with cancer (in some embodiments, the same animal model for cancer) administered a negative control as measured using assays well known in the art. In another embodiment, the administration of a cancer vaccine described herein or a composition comprising a cancer vaccine described herein to a subject with (in some embodiments, an animal model for cancer) reduces the size of a tumor by at least 10%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%, or 10% to 25%, 25% to 50%, 25% to 75%, 50% to 75%, 75% to 100% relative to the growth of a tumor in a subject with cancer (in some embodiments, the same animal model for cancer) administered a negative control as measured using assays well known in the art.

In some embodiments, a cancer vaccine described herein is administered to a subject in combination with one or more other therapies, e.g., anti-cancer agents, cytokines, cellular vaccines or anti-hormonal agents, to treat and/or manage cancer. In one embodiment, the combination of a cancer vaccine described herein and one or more other therapies provides an additive therapeutic effect relative to the therapeutic effects of the cancer vaccine described herein alone or the one or more other therapies alone. In another embodiment, the combination of a cancer vaccine described herein and one or more other therapies provides more than an additive therapeutic effect relative to the therapeutic effects of the cancer vaccine described herein alone or the one or more other therapies alone. In a specific embodiment, the combination of a cancer vaccine described herein and one or more other therapies provides a synergistic therapeutic effect relative to the therapeutic effects of the cancer vaccine described herein alone or the one or more other therapies alone.

In a specific embodiment, a cancer vaccine described herein is administered in combination with radiation therapy comprising, e.g., the use of x-rays, gamma rays and other sources of radiation to destroy the cancer cells. In specific embodiments, the radiation treatment is administered as external beam radiation or teletherapy wherein the radiation is directed from a remote source. In other embodiments, the radiation treatment is administered as internal therapy or brachytherapy wherein a radioactive source is placed inside the body close to cancer cells or a tumor mass. In one aspect, the cancer vaccine described herein can activate or enhance the immune function of cancer patient with a compromised immune system due to anti-cancer therapy. In another embodiment, a cancer vaccine described herein is administered in combination with chemotherapy. In an embodiment, a cancer vaccine described herein can be used before, during or after radiation therapy or chemotherapy. In another embodiment, a cancer vaccine described herein can be used before, during or after surgery.

5.8.1 Types of Cancers

Cancers and related disorders that can be treated, protected against, or managed in accordance with the methods described herein include, but are not limited to, the following: leukemias including, but not limited to, acute leukemia, acute lymphocytic leukemia, acute myelocytic Leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, and chronic lymphocytic leukemia, hairy cell leukemia; polycythemia vera; lymphomas such as but not limited to Hodgkin's disease, and non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, and synovial sarcoma; brain tumors including but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma; breast cancer including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including but not limited to, pheochromocytoma and adrenocortical carcinoma; thyroid cancer such as but not limited to papillary or follicular thyroid cancer, medullary thyroid cancer and anaplastic thyroid cancer; pancreatic cancer, including but not limited to, insulinoma, gastrinoma, glucagonoma, vipoma, somatostatin-secreting tumor, and carcinoid or islet cell tumor; pituitary cancers including but not limited to, Cushing's disease, prolactin-secreting tumor, acromegaly, and diabetes insipius; eye cancers including but not limited to, ocular melanoma such as iris melanoma, choroidal melanoma, and cilliary body melanoma, and retinoblastoma; vaginal cancers, including but not limited to, squamous cell carcinoma, adenocarcinoma, and melanoma; vulvar cancer, including but not limited to, squamous cell carcinoma, melanoma, adenocarcinoma, basal cell carcinoma, sarcoma, and Paget's disease; cervical cancers including but not limited to, squamous cell carcinoma, and adenocarcinoma; uterine cancers including but not limited to, endometrial carcinoma and uterine sarcoma; ovarian cancers including but not limited to, ovarian epithelial carcinoma, borderline tumor, germ cell tumor, and stromal tumor; esophageal cancers including but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers including but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers including but not limited to hepatocellular carcinoma and hepatoblastoma; gallbladder cancers including but not limited to, adenocarcinoma; cholangiocarcinomas including but not limited to, pappillary, nodular, and diffuse; lung cancers including but not limited to, non-small cell lung cancer, squamous cell carcinoma (epidermoid carcinoma), adenocarcinoma, large-cell carcinoma and small-cell lung cancer; testicular cancers including but not limited to, germinal tumor, semi noma, anaplastic, spermatocytic, nonseminoma, embryonal carcinoma, teratoma carcinoma, choriocarcinoma (yolk-sac tumor); prostate cancers including but not limited to, adenocarcinoma, leiomyosarcoma, and rhabdomyosarcoma; penal cancers; oral cancers including but not limited to, squamous cell carcinoma; basal cancers; salivary gland cancers including but not limited to, adenocarcinoma, mucoepidermoid carcinoma, and adenoidcystic carcinoma; pharynx cancers including but not limited to, squamous cell cancer, and verrucous; skin cancers including but not limited to, basal cell carcinoma, squamous cell carcinoma and melanoma, and superficial spreading melanoma, nodular melanoma, lentigo malignant melanoma, acral lentiginous melanoma; kidney cancers including but not limited to, renal cell cancer, renal cancer, adenocarcinoma, hypernephroma, fibrosarcoma, and transitional cell cancer (renal pelvis and/or uterer); Wilms' tumor; bladder cancers including but not limited to, transitional cell carcinoma, squamous cell cancer, adenocarcinoma, and carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

In one embodiment, the cancer is benign, e.g., polyps and benign lesions. In other embodiments, the cancer is metastatic. The cancer vaccine can be used in the treatment of pre-malignant as well as malignant conditions. Pre-malignant conditions include hyperplasia, metaplasia, and dysplasia. Treatment of malignant conditions includes the treatment of primary as well as metastatic tumors. In one embodiment, the cancer is a solid tumor. In a specific embodiment the cancer is melanoma, colon cancer, prostate cancer, ovarian cancer, pancreatic cancer, lung cancer, rhabdomyosarcoma, neuroblastoma, Ewing sarcoma, gastric cancer, or hepatoma.

5.8.2 Patient Populations

In some embodiments, a cancer vaccine described herein, compositions comprising a cancer vaccine described herein, or combination therapies are administered to a subject suffering from or diagnosed with cancer. In other embodiments, a cancer vaccine described herein, compositions comprising a cancer vaccine described herein, or combination therapies are administered to a subject predisposed or susceptible to developing cancer. In some embodiments, a cancer vaccine described herein, compositions comprising a cancer vaccine described herein, or combination therapies are administered to a subject that lives in a region where there is a high occurrence rate of cancer. In a specific embodiment, the cancer is characterized by a pre-malignant tumor or a malignant tumor.

In some embodiments, a cancer vaccine described herein, composition comprising a cancer vaccine described herein, or a combination therapy is administered to a mammal. In certain embodiments, a cancer vaccine described herein, composition comprising a cancer vaccine described herein, or a combination therapy is administered to a mammal which is 0 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In certain embodiments, a cancer vaccine described herein, composition comprising a cancer vaccine described herein, or a combination therapy is administered to a pet, e.g., a dog or cat. In certain embodiments, a cancer vaccine described herein, composition comprising a cancer vaccine described herein, or a combination therapy is administered to a farm animal or livestock, e.g., pig, cows, horses, chickens, etc.

In certain embodiments, a cancer vaccine described herein, composition comprising a cancer vaccine described herein, or a combination therapy is administered to a human at risk developing cancer. In certain embodiments, a cancer vaccine described herein, composition comprising a cancer vaccine described herein, or a combination therapy is administered to a human with cancer. In certain embodiments, a cancer vaccine described herein, composition comprising a cancer vaccine described herein, or a combination therapy is administered to a human diagnosed with cancer. In certain embodiments, the patient is a human 0 to 6 months old, 6 to 12 months old, 1 to 5 years old, 5 to 10 years old, 5 to 12 years old, 10 to 15 years old, 15 to 20 years old, 13 to 19 years old, 20 to 25 years old, 25 to 30 years old, 20 to 65 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old.

In certain embodiments, a cancer vaccine described herein, composition comprising a cancer vaccine described herein, or a combination therapy is administered to a subject that has or is at risk of getting AIDS, a viral infection, or a bacterial infection. In certain embodiments, a subject that is, will or has undergone surgery, chemotherapy and/or radiation therapy.

In some embodiments, a patient is administered a cancer vaccine described herein, composition comprising a cancer vaccine described herein, or a combination therapy is before any adverse effects or intolerance to therapies other than a cancer vaccine described herein develops. In some embodiments, a cancer vaccine described herein, compositions comprising a cancer vaccine described herein, or combination therapies are administered to refractory patients. In a certain embodiment, refractory patient is a patient refractory to a standard anti-cancer therapy. In certain embodiments, a patient with cancer is refractory to a therapy when the cancer has not significantly been eradicated and/or the symptoms have not been significantly alleviated. The determination of whether a patient is refractory can be made either in vivo or in vitro by any method known in the art for assaying the effectiveness of a treatment, using art-accepted meanings of "refractory" in such a context. In various embodiments, a patient with cancer is refractory when a cancerous tumor has not decreased or has increased.

In some embodiments, a cancer vaccine described herein, compositions comprising a cancer vaccine described herein, or combination therapies are administered to a patient to protect against the onset or reoccurrence of cancer in a patient at risk of developing such cancer. In some embodiments, a cancer vaccine described herein, compositions comprising a cancer vaccine described herein, or combination therapies are administered to a patient who is susceptible to adverse reactions to conventional therapies.

In some embodiments, a cancer vaccine described herein, compositions comprising a cancer vaccine described herein, or combination therapies are administered to a patient who has proven refractory to therapies other than a cancer vaccine described herein, but are no longer on these therapies. In certain embodiments, the patients being managed or treated in accordance with the methods described herein are patients already being treated with antibiotics, anti-cancer agents, or other biological therapy/immunotherapy. Among these patients are refractory patients, patients who are too young for conventional therapies, and patients with reoccurring viral infections despite management or treatment with existing therapies.

In some embodiments, the subject being administered a cancer vaccine described herein, compositions comprising a cancer vaccine described herein, or combination therapies has not received a therapy prior to the administration of the cancer vaccine described herein, compositions comprising a cancer vaccine described herein, or combination therapies. In other embodiments, a cancer vaccine described herein, compositions comprising a cancer vaccine described herein, or combination therapies are administered to a subject who has received a therapy prior to administration of one or more a cancer vaccine described herein, compositions comprising a cancer vaccine described herein, or combination therapies. In some embodiments, the subject administered a cancer vaccine described herein or a composition comprising a cancer vaccine described herein was refractory to a prior therapy or experienced adverse side effects to the prior therapy or the prior therapy was discontinued due to unacceptable levels of toxicity to the subject.

5.9 Administration and Dosage 5.9.1 Mode of Administration

A cancer vaccine described herein or composition thereof can be administered via any route known in the art. A cancer vaccine described herein or compositions thereof can be administered by, for example, infusion or bolus injection, and may be administered together with another biologically active agent. Administration can be systemic or local. Various delivery systems are known and can be used to deliver a cancer vaccine described herein or compositions thereof.

Methods of administration include but, are not limited to, parenteral, intradermal, intramuscular, intraperitoneal, intravenous, subcutaneous, intracerebral, or intratumorally. In a specific embodiment, the cancer vaccine is intravenously, intradermally or subcutanouesly administered to the patient. In another specific embodiment, the cancer vaccine is administered to the patient by direct intranodal delivery. In another specific embodiment, the cancer vaccine is administered to the tumor itself. The mode of administration is left to the discretion of the practitioner.

In specific embodiments, it may be desirable to administer a cancer vaccine or composition thereof locally. This may be achieved, for example, and not by way of limitation, by local infusion or by means of an implant, said implant being of a porous or gelatinous material, including membranes, such as sialastic membranes, or fibers.

5.9.2 Dosage

The amount of a cancer vaccine described herein, or the amount of a composition comprising a cancer vaccine described herein, that will be effective in the treatment of, protection against, and/or management of cancer can be determined by standard clinical techniques. In vitro or in vivo assays may optionally be employed to help identify optimal dosage ranges. The precise dose to be employed will also depend, e.g., on the route of administration, the type of symptoms, and the seriousness of the symptoms, and should be decided according to the judgment of the practitioner and each patient's or subject's circumstances.

Doses of pulsed-dendritic cells described herein for administration by any route of administration can be at least 100, 200, 300, 400, 500, 700, 1,000, 5,000, 10,000, 25,000, 50,000, or 100,000 cells. In specific embodiments, the number of pulsed-dendritic cells is at least 100, 200, 300, 400, 500 cells. In other embodiments, the number of pulsed-dendritic cells is at least 300, 400, 500, 700, 1,000 cells. In yet other specific embodiments, the number of pulsed-dendritic cells is at least 700, 1,000, 5,000, 10,000 cells. In some embodiments, the number of pulsed-dendritic cells is at least 5,000, 10,000, 25,000, 50,000, or 100,000 cells. In yet another embodiment, the number of cells is at least 50,000, or 100,000 cells. In other embodiments, the number of pulsed-dendritic cells is at least $1\times10^6$, $5\times10^6$, $1\times10^7$, $5\times10^7$, $1\times10^8$, $5\times10^8$ or more cells. In specific embodiments, the number of pulsed-dendritic cells is between $1\times10^2$ to $1\times10^4$, $5\times10^4$ to $5\times10^6$, $1\times10^5$ to $1\times10^7$, $1\times10^5$ to $5\times10^8$, $1\times10^6$ to $1\times10^8$, or $1\times10^6$ to $1\times10^7$, or $1\times10^4$ to $1\times10^5$ cells.

In certain embodiments, a subject is administered a cancer vaccine described herein or composition thereof in an amount effective to inhibit or reduce symptoms associated with cancer by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In certain embodiments to treat, a subject is administered a cancer vaccine described herein or a composition thereof in an amount effective to inhibit or reduce symptoms associated with cancer by at least 1.5-fold, 2-fold, 2.5-fold, 3-fold, 4-fold, 5-fold, 8-fold, 10-fold, 15-fold, 20-fold, or 2- to 5-fold, 2- to 10-fold, 5- to 10-fold, or 5- to 20-fold relative to a negative control as determined using an assay described herein or other known to one of skill in the art.

In certain embodiments, to treat, protect against, and/or manage cancer, a subject is administered a cancer vaccine described herein or composition thereof in an amount effective to inhibit or reduce tumor growth or cancer cell proliferation by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In some embodiments, a subject is administered a cancer vaccine described herein or composition thereof in an amount effective to inhibit or reduce tumor growth or cancer cell proliferation by at least 1.5-fold, 2-fold, 2.5-fold, 3-fold, 4-fold, 5-fold, 8-fold, 10-fold, 15-fold, 20-fold, or 2 to 5-fold, 2 to 10-fold, 5 to 10-fold, or 5 to 20-fold relative to a negative control as determined using an assay described herein or others known to one of skill in the art.

In certain embodiments to, a subject is administered a cancer vaccine described herein or composition thereof in an amount effective to induce or enhance an immune response by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In some embodiments, a subject is administered a cancer vaccine described herein or composition thereof in an amount effective to induce or enhance an immune response by at least 1.5-fold, 2-fold, 2.5-fold, 3-fold, 4-fold, 5-fold, 8-fold, 10-fold, 15-fold, 20-fold, or 2 to 5-fold, 2 to 10-fold, 5 to 10-fold, or 5 to 20-fold relative to a negative control as determined using an assay described herein or others known to one of skill in the art.

In certain embodiments to, a subject is administered a cancer vaccine described herein or composition thereof in an amount effective to increase or enhance the number of lymphocytes (in some embodiments, in a specific target body compartment) by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In some embodiments, a subject is administered a cancer vaccine described herein or composition thereof in an amount effective to increase or enhance the number of lymphocytes (in some embodiments, in a specific target body compartment) by at least 1.5-fold, at least 2-fold, at least 2.5-fold, at least 3-fold, at least 4-fold, at least 5-fold, at least 8-fold, at least 10-fold, at least 15-fold, or at least 20-fold; or by approximately 2 to 5-fold, 2 to 10-fold, 5 to 10-fold, or 5 to 20-fold relative to a negative control as determined using an assay described herein or others known to one of skill in the art. In some embodiments, the specific target body compartment where the number of lymphocytes is increased or enhanced by a cancer vaccine described herein is the lung, stomach, heart, kidney, liver, small intestines, large intestines, breast, prostate, or bladder. In particular embodiments, the specific target body compartment where the number of lymphocytes is increased or enhanced is the body compartment affected by cancer. In some embodiments, the specific target body compartment where the number of lymphocytes is increased or enhanced is the lymph node, spleen, or peripheral blood.

In certain embodiments, a dose of a cancer vaccine described herein or composition thereof is administered to a subject every day, every other day, every couple of days, every third day, once a week, twice a week, three times a week, or once every two weeks or once a month, or less. In other embodiments, two, three or four doses of a cancer vaccine described herein or composition thereof is administered to a subject every day, every couple of days, every third day, once a week or once every two weeks. In some embodiments, a dose(s) of a cancer vaccine described herein or composition thereof is administered for 2 days, 3 days, 5 days, 7 days, 14 days, or 21 days. In certain embodiments, a dose of a cancer vaccine described herein or composition thereof is administered for 1 month, 1.5 months, 2 months, 2.5 months, 3 months, 4 months, 5 months, 6 months or more.

In a preferred embodiment, a patient is administered multiple doses of a cancer vaccine, wherein each dose of the cancer vaccine comprises dendritic cells pulsed with cancer cells undergoing ICD which had been cryopreserved and thawed. In a specific embodiment, a batch of dendritic cells (which had been pulsed with cancer cells which had been induced to undergo ICD and cryopreserved) is frozen and stored in separate containers (e.g., 2, 3, 4, 5, 6, 7, 8, 9, 10, 11, 12, 13, 14, 15, 16, 17, 18, 19, 20 or more containers, such as vials) and one container such as a vial, or optionally more than 1 container, is thawed for delivery of the cancer vaccine to a patient. This allows for standardization of the manufacturing process for the dendritic cell vaccine so that two or more patients may be treated with vaccines produced from the same batch of cryopreserved cancer cells undergoing ICD.

The dosages of prophylactic or therapeutic agents which have been or are currently used for the treatment of, protection against, and/or management of cancer can be determined using references available to a clinician such as, e.g., the Physicians' Desk Reference (67th ed. 2013). In a specific embodiment, dosages lower than those which have been or are currently being used to treat, protect against, and/or manage cancer are utilized in combination with a cancer vaccine described herein or compositions thereof.

The above-described administration schedules are provided for illustrative purposes only and should not be considered limiting.

5.10 Biological Assays

The antigen presenting capability of pulsed dendritic cells can be assessed using techniques known to one skilled in the art. Various assays known in the art can be used to assess whether a cancer vaccine described herein activates or enhances an immune function. In one aspect, a cancer vaccine described herein increases an immune response that can be, e.g., an antibody response (humoral response) or a cellular immune response, e.g., cytokine secretion (e.g., interferon), chemokine secretion, helper activity or cellular cytotoxicity. In a specific embodiment, the ability of pulsed dendritic cells to induce IFN-gamma production of lymphocytes is assessed.

Proliferation of certain immune cells (e.g., lymphocytes) may be assessed by $^3$H-thymidine incorporation. The cytotoxicity of T cells can be tested in a $^{51}$Cr-release assay as described in the art.

An ELISPOT assay can be used to measure cytokine release by lymphocytes co-cultured by pulsed dendritic cells described herein. Cytokine secretion can be detected by antibodies which are specific for a particular cytokine, e.g., interleukin-2, tumor necrosis factor-α or interferon-γ, or chemokine. In a specific embodiment, a cytokine secretion by a cancer vaccine can be assessed using the techniques described in Section 6, infra.

In specific embodiments, a cancer vaccine described herein induces or enhances lymphocyte cell proliferation in a subject that by at least 0.2 to 5 times, 5 to 20 times, 10 to 30 times, 20 to 50 times, 50 to 200 times, 100 to 500, 200 to 1000 times, or 500 to 2,000 times higher relative to lymphocyte cell proliferation in a negative control. In specific embodiments, a cancer vaccine described herein induces or enhances T cell proliferation in a subject that by at least 0.2 to 5 times, 5 to 20 times, 10 to 30 times, 20 to 50 times, 50 to 200 times, 100 to 500, 200 to 1000 times, or 500 to 2,000 times higher relative to T cell proliferation in a negative control as determined by methods well known in the art, e.g., flow cytometry, CSFE staining, $^3$H-thymidine incorporation.

5.11 Methods for Producing Vaccines for Immunotherapy

In certain embodiments, dendritic cells are pulsed with the animal cells that express an antigen(s) of interest and are undergoing ICD, and the pulsed dendritic cells are the vaccine administered to a patient. In a preferred embodiment, the cells undergoing ICD were cryopreserved and thawed before being used to pulse dendritic cells. In a specific embodiment, the pulsed dendritic cells are autologous to the patient receiving the vaccine.

In some embodiments, dendritic cells are pulsed with the animal cells that express an antigen(s) of interest and are undergoing ICD, the pulsed dendritic cells are co-cultured with lymphocytes (e.g., T lymphocytes) and the lymphocytes are administered to a patient as the vaccine. In a specific embodiment, the pulsed dendritic cells and the lymphocytes are autologous to the patient receiving the cancer vaccine.

Techniques known to one skilled in the art can be used to pulse dendritic cells with cancer cells undergoing ICD. Further, techniques known to one skilled in the art can be used to co-culture lymphocytes with pulsed dendritic cells.

5.12 Kits

Provided herein is a pharmaceutical pack or kit comprising one or more containers comprising cryopreserved cells undergoing ICD. Optionally associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical pack or kit may include instructions for use of the cryopreserved cells described herein. The kits encompassed herein can be used in the above methods.

In a specific embodiment, a pharmaceutical pack or kit comprises 1, 2, 3, 4, 5, 6, 7, 8, 9, 10, 11, 12, 13, 14, 15, 16, 17, 18, 19, 20 or more containers (e.g., vials) containing cryopreserved cancer cells undergoing ICD. In a particular embodiment, each container contains cryopreserved cancer cells all from the same batch of cancer cells induced to undergo ICD. In certain embodiments, each container (e.g., a vial) of cryopreserved cancer cells contains 100, 150, 200, 250, 300, 350, 400, 450, 500, 550, 600, 650, 700, 750, 800, 850, 900, 950 or 1000 cancer cells induced to undergo ICD. In some embodiments, each container (e.g., a vial) of cryopreserved cancer cells contains $1\times10^2$, $5\times10^2$, $1\times10^3$, $5\times10^3$, $1\times10^4$, $5\times10^4$, $1\times10^5$, $5\times10^5$, $1\times10^6$, $5\times10^6$, $1\times10^7$, $5\times10^7$ or $1\times10^8$ cancer cells induced to undergo ICD. In certain embodiments, each container (e.g., a vial) of cryopreserved cancer cells contains $1\times10^1$ to $1\times10^2$, $1\times10^2$ to $5\times10^2$, $1\times10^2$ to $1\times10^3$, $1\times10^3$ to $5\times10^3$, $1\times10^2$ to $1\times10^4$, $1\times10^3$ to $5\times10^4$, $1\times10^3$ to $1\times10^4$, $1\times10^2$ to $1\times10^5$, $1\times10^2$ to $5\times10^5$, $1\times10^2$ to $1\times10^6$, $1\times10^3$ to $5\times10^6$, $1\times10^4$ to $1\times10^7$, $1\times10^5$ to $1\times10^7$, $1\times10^5$ to $1\times10^7$, $1\times10^6$ to $1\times10^8$, $1\times10^7$ to $1\times10^8$ cancer cells induced to undergo ICD.

In another embodiment, approximately 55%, approximately 60%, approximately 65%, approximately 70%, approximately 75%, approximately 80%, approximately 85%, approximately 90%, approximately 95% or approximately 98% of cryopreserved cancer cells undergoing ICD in a container (e.g., a vial) maintain one, two, three or more, or all of the characteristics and/or functions of non-cryopreserved/thawed cancer cells induce to undergo ICD after thawing as assessed by techniques described herein (e.g., in Section 5.2, 5.5, and 6) and/or known to one skilled in the art. In another specific embodiment, approximately 55%, approximately 60%, approximately 65%, approximately 70%, approximately 75%, approximately 80%, approximately 85%, approximately 90%, approximately 95% or approximately 98% of the cryopreserved cancer cells in a container (e.g., a vial) express ICD markers after thawing. In some embodiments, approximately 55% to approximately 65%, approximately 65% to approximately 85%, or approximately 75%, to approximately 85%, approximately 80% to approximately 90% or approximately 90% to approximately 95% of cryopreserved cancer cells undergoing ICD in a container (e.g., a vial) maintain one, two, three or more, or all of the characteristics and/or functions of non-cryopreserved/thawed cancer cells induce to undergo ICD after thawing as assessed by techniques described herein (e.g., in Section 5.2, 5.5, and 6) and/or known to one skilled in the art.

In a specific embodiment, at least 50% of the cryopreserved cancer cells in a container (e.g., a vial) express markers of ICD after thawing. In specific embodiments, approximately 55%, approximately 60%, approximately 65%, approximately 70%, approximately 75%, approximately 80%, approximately 85%, approximately 90%, approximately 95% or approximately 98% of the cryopreserved cancer cells in a container (e.g., a vial) express ICD markers after thawing. In some embodiments, approximately 55% to approximately 65%, approximately 65% to approximately 85%, or approximately 75%, to approximately 85%, approximately 80% to approximately 90% or approximately 90% to approximately 95% of the cryopreserved cancer cells in a container (e.g., a vial). In a specific embodiment, the expression of ICD markers, such as HSP70, HSP90 and calreticulin, by cryopreserved cancer cells undergoing ICD after thawing is not significantly altered relative to non-cryopreserved/thawed cancer cells induced to undergo ICD.

6. EXAMPLES

This example demonstrates that HHP treated and cryopreserved cancer cells are a reliable and potent source of tumor antigens for immunotherapy protocols. The HHP-frozen cancer cell death fulfills all currently described criteria of immunogenic cell death, including the preferentially activation of apoptotic pathway. The HHP-frozen cancer cells carry sufficient amount of tumor associated antigens, such as PSA, PSMA, and Her2/Neu. Further, the HHP-frozen cancer cells are able to activate dendritic cells and induce an extended level of antigen specific T cell response.

6.1 Materials & Methods
Cell Line:
Prostate cancer cells (LNCap; HLA-A2 positive; ATCC) and ovarian cancer cells (SKOV3; HLA-A2 positive; ATCC) were cultured in RPMI 1640 medium (Gibco). Medium was supplemented with 10% heat-inactivated fetal bovine serum (PAA), 100 U/ml penicillin and 2 mmol/L L-glutamine.

Antibodies and Reagents:
The following monoclonal antibodies (mAbs) against the indicated molecules were used: CD80-FITC, CD83-PE, CD86-PE-Cy5, CD14-PE-Dy590, CD8-PE-Dy590 (Exbio), CD11c-PE, HLA-DR-Alexa700, IFNγ-FITC, CD4-PC7 (BD Bioscineces), anti-HSP70 (R&D), anti-HSP90, anti-calreticulin (Enzo), anti-PSA, GAPDH (Genetex), anti-PSMA (Abcam) and anti-Her2/Neu (Genetex).

Apoptosis Induction and Detection:
Tumor cell death was induced by HHP treatment (250 MPa, 10 mins.). Cell death was assessed by annexin V fluorescein isothiocyanate staining Briefly, $2 \times 10^5$ cells per sample were collected, washed in PBS, pelleted, and resuspended in an incubation buffer containing annexin V Dy647 (Exbio). The samples were kept in the dark and incubated for 15 min before the addition of DAPI and subsequent analysis on FACS Fortessa (BD Bioscience) using FlowJo software.

Flow Cytometric Analysis of HSP70, HSP90 and CRT:
A total of $1 \times 10^5$ cells were plated in 12-well plates and treated by HHP for 6, 12 or 24 h. The cells were collected and washed twice with PBS. The cells were incubated for 30 min with primary antibody, followed by washing and incubation with the Alexa 648-conjugated monoclonal secondary antibody in a blocking solution. Each sample was then analyzed by FACScan Fortessa (BD Bioscience) to identify expression of HSP70, HSP90 and CRT.

Immunofluorescence of HSP70, HSP90 and CRT by Confocal Microscopy:
The cells were collected and washed twice with PBS. The cells were then incubated for 30 min with primary antibody diluted in cold blocking buffer (2% fetal bovine serum in PBS), followed by washing and incubation with the Alexa Fluor 488 goat anti-mouse secondary antibody. Cells were washed twice with PBS and fixed in 4% paraformaldehyde in PBS for 20 min and mounted on slides. The emission spectra of green HSP70, HSP90 or CRT were detected in the 500-550 nm range. Cells were examined under a DMI 6000 inverted Leica TCS AOBS SP5 tandem scanning confocal microscope with an AR (488 nm) laser and an x63 oil immersion objective.

Generation of Dendritic Cells:
Immature monocyte-derived DCs (moDCs) were generated as previously described. Briefly, peripheral blood mononuclear cells (PBMCs) were isolated from buffy coats of healthy HLA-A2$^+$ or HLA-A2$^-$ donors by Ficoll-Paque PLUS gradient centrifugation (GE Healthcare, Uppsala, Sweden) and monocytes were isolated by plastic adherence after 2 h of cell adhesion ($75 \times 10^6$ PBMCs) in Nunclon 75-cm2 culture flasks (Nunc). Adherent monocytes were subsequently cultured for 6 days in serum free CellGro DC media (CellGenix) in the presence of GM-CSF (Gentaur) at a concentration of 500 U/ml and 20 ng/ml of IL-4 (Gentaur). After 3 days of culture, fresh CellGro and cytokines were added to the culture flasks. After 6 days, immature DCs were seeded in Nunclon 48-well plates ($5 \times 10^5$ DCs in 500 µl of CellGro supplemented with cytokines per well) and pulsed with apoptotic LNCap cells for 4 h, furthermore DC were matured by Poly (I:C) (InvivoGen) at 25 µg/ml or LPS (Sigma-Aldrich) at 1 µg/ml. Immature and mature DCs were used for further studies. For cocultures, a fraction of the PBMCs was cryopreserved, thawed and used for generation of DCs for restimulation. Non-adherent monocyte-depleted PBMCs were frozen and used as lymphocytes for cocultures with DCs.

Flow Cytometry:
Immature and mature DCs were phenotyped using the following monoclonal antibodies: CD80-FITC, CD86-PE, CD83-PE-Cy5 (Beckman Coulter), CD14-PE-Dy590, CD11c-APC (Exbio) and HLA-DR-PE-Cy7 (BD Biosciences). The cells were stained for 20 min at 4° C., washed twice in PBS and analyzed using LSRFortessa (BD Biosciences) with FlowJo software (Tree Star). DCs were gated according to their FSC and SSC properties and as CD11c positive cells. Only viable DCs (DAPI negative cells) were included in the analysis. DAPI was purchased from Invitrogen.

FACS Analysis of DC Phenotype after Interaction with Killed Tumor Cells:
The phenotype of DCs cultured with tumor cells was monitored by flow cytometry. Tumor cells were killed by HHP and were cocultured for 24 h with immature DCs. For some experiments, the DCs and tumor cells were dye-labeled before coculture to monitor phagocytosis. Monoclonal antibodies (mAbs) against the following molecules were used: CD80-A700 (Exbio), CD83-PerCP-Cy5,5 (BioLegend), CD86-A647 (BioLegend), CD14-PE (Exbio), CD11c-APC (Exbio), HLA-DR PC7 (BD Biosciences).

The DCs were stained for 30 minutes at 4° C., washed twice in phosphate-buffered saline (PBS) and analyzed using FACS Aria (BD Biosciences) using FlowJo software. The DCs were gated according to the FSC and SSC properties.

The appropriate isotype controls were included, and 50000 viable DCs were acquired for each experiment.

Uptake of HHP-Treated Cancer Cells by DCs:

For flow cytometry analysis of phagocytosis, tumor cells were harvested and labeled with Vybrant DiD cell labeling solution (Invitrogen). To prepare HHP treated cells, stained LNCap cells were seeded in CellGro media in Nunclon 25-cm$^2$ culture flasks (Nunc) at a concentration of $4\times10^5$ cells/ml and subjected to a 250 MPa of HHP for 10 minutes to induce apoptosis. Cells were then incubated for 24 h at 37° C. with 5% CO2 before use. To determine the uptake of HHP-treated tumor cells by DCs, immature DCs were stained with Vybrant DiO cell labeling solution (Invitrogen) and cocultured with LNCap cells at a cell ratio of 5:1 in Nunclon U-bottom 96-well plates (Nunc) for 24 h at 37° C. with 5% $CO_2$. Parallel control cultures were set up for 24 h on ice to evaluate the passive transfer of dye or labeled tumor fragments to DCs. The phagocytic ability of DCs was evaluated by flow cytometry.

Expansion of Antigen-Specific T-Lymphocytes and Intracellular IFN-γ Staining:

Immature DCs were fed tumor cells at a DC/tumor cell ratio of 5:1 for 24 hours. In some experiments pulsed DCs were stimulated with Poly (I:C) (25 μg/ml). Non adherent peripheral blood lymphocytes (PBL) ($2\times10^5$ in RPMI-1640+ 10% AB human serum (Invitrogen)) and the mature pulsed DCs ($4\times10^4$ in CellGro) were cocultured at a ratio of 5:1 in U-bottom 96-well plates for 7 days. A total of 20 U/ml of IL-2 (PeproTech) was added on days 3 and 5. On day 7, the lymphocytes were restimulated with fresh tumor cells pulsed DCs, and the frequency of antigen-specific T cells was determined using intracellular staining for IFN-γ. Brefeldin A (BioLegend) was added to block the extracellular release of IFN-γ one hour and a half after restimulation. After 3 h of incubation with Brefeldin A, the cells were washed in PBS, stained with anti-CD3-PerCP-Cy5.5 (eBioscience) and CD8-PE-Dy590 antibody (Exbio), fixed using Fixation Buffer (eBioscience), permeabilized with Permeabilization Buffer (eBioscience) and stained using anti-IFN-γ-FITC antibody (BD Biosciences). The cells were acquired using the LSRFortessa (BD Biosciences) and analyzed with FlowJo software (Tree Star).

Preparation of Cell Extracts and Western Immunoblot Analysis:

Cell extracts were prepared at the indicated time points following HHP treatment. After treatment cells were washed with ice-cold PBS and lysed on ice in RIPA buffer (10 mM TRIS pH7.5, 150 mM NaCl, 5 mM EDTA, 1% Triton X 100)+protease inhibitor cocktail (Roche Diagnostics) and 1 mM PMSF (phenylmethylsulfonyl fluoride). Proteins were separated by 12% SDS-PAGE and transferred to nitrocellulose membrane (Bio-Rad). The membranes were blocked in 5% nonfat dry milk in TBST buffer (50 mM Tris, 150 mM NaCl, 0.05% Tween 20) for 1 h at room temperature and incubated with primary antibody overnight at 4° C. The membranes were then washed in TBST and incubated for 1 h at room temperature with horseradish peroxidase-conjugated secondary antibodies. Detection was carried out with the enhanced chemiluminescence (ECL) detection system. Equal protein loading was ensured by BCA assay, verified by analysis of Ponceau-S staining of the membrane and GADPH reprobing.

Statistical Analysis:

The data were analyzed by One-Way ANOVA with Dunnett's multiple comparison post hoc test and Student's unpaired two-tailed t test using GraphPad Prism 5 (San Diego, Calif., USA). The results were considered statistically significant when $p<0.05$.

6.2 Results

Figure 1B:
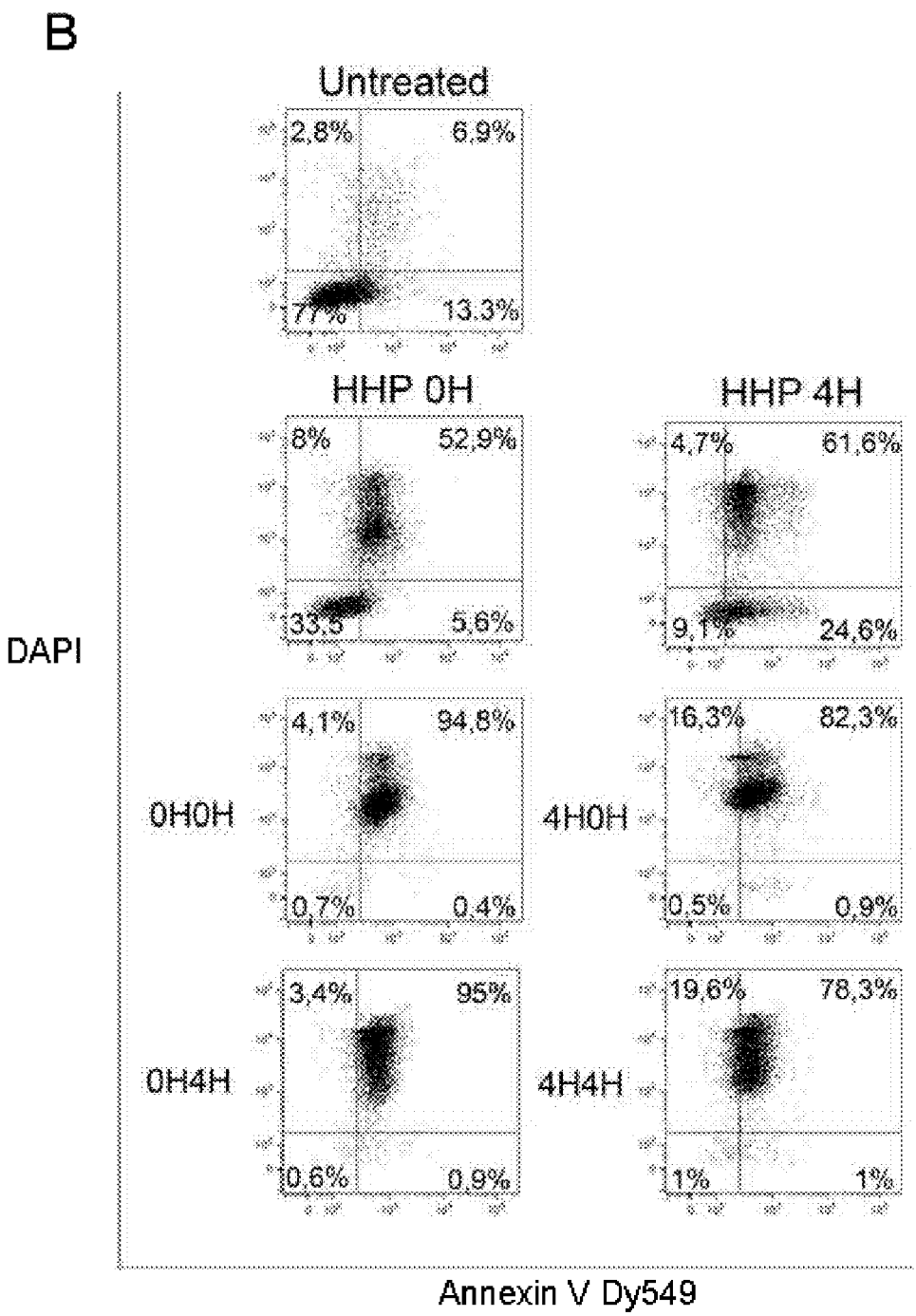

Cryopreservation of HHP Treated Tumor Cells Preserves the Apoptotic Character of Cell Death and the Expression of Immunogenic Cell Death Markers:

To initially determine the ability of HHP-treated and frozen tumor cells to preserve features of immunogenic cell death, the prostate cancer cell line LNCap and ovarian cancer cell line SKOV3 were used. To verify whether HHP treated frozen cancer cells die by apoptosis or necrosis, tumor cells were treated by 250 MPa for 10 min and frozen for minimal course of 1 week and thawed. Cell death was analyzed according to DAPI and annexin V staining (FIG. 1A, B). Treatment of both LNCap and SKOV3 cells with HHP led to the apoptosis (% annexin V+ cells) of more than 50% immediately after the treatment with the majority of cells demonstrating a staining pattern typical of apoptosis (annexin V+) rather than necrosis (annexinV-/DAPI+) (FIG. 1B). Furthermore, the apoptosis of frozen-HHP cells was evaluated. Cells frozen in time 0H and 4H after the HHP-treatment and determined in 0H and 4H timepoints are dying preferentially in apoptotic way with more than 90% of Annexin V+/DAPI+ cells (FIG. 1A, B).

Expanded tumor cells were collected from culture flasks by using trypsin. Detached cells were centrifuged and washed with PBS+EDTA multiple times. The viability of the cells was assessed by microscopy using a 0.4% trypan blue solution. Cells were resuspended in growth media and immunogenic cell death was induced by HHP. Following HHP the state of the cells was assessed by microscopy and incubated in growth media for 2 hours in a $CO_2$ incubator at 37° C. After incubation, the cells were collected, washed, resuspended in freezing medium CryoStor CS10 and aliquoted in freezing vials ($20\times10^6$ cells for vial, 1 ml per vial). Freezing was done by placing the vials at −80° C. overnight in a isopropanol container to ensure slow freezing. The next day the vials were transferred into a liquid nitrogen tank. Cells were thawed prior to incubation with DCs. The cells were thawed in the palm of the hand or in an incubator at 37° C. in order to assure a quick thaw and resuspended in warm growth media.

Figure 1C:
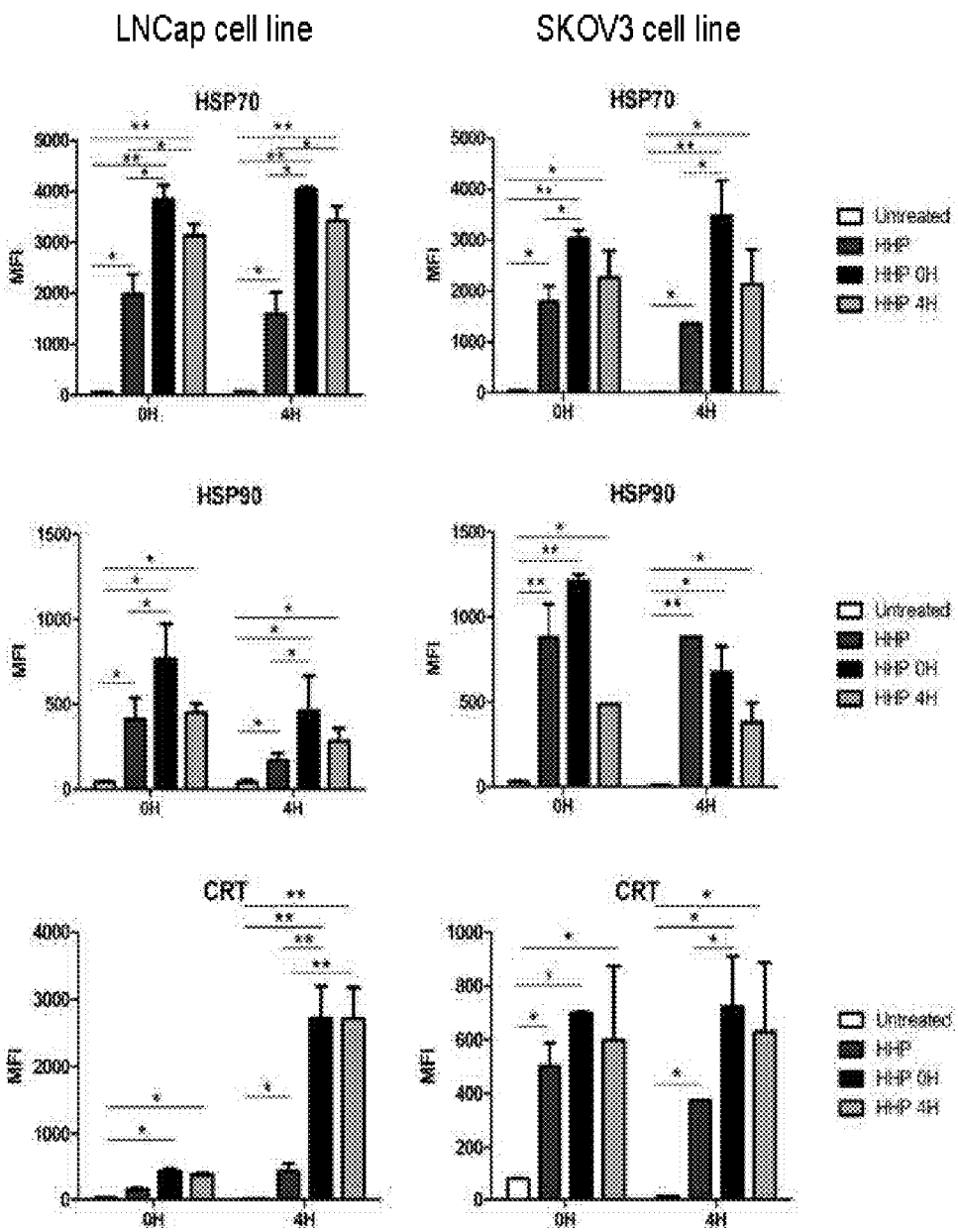

The kinetics of the expression of immunogenic cell death markers on tumor cells undergoing apoptosis induced by HHP and HHP-frozen in time 0H and 4H was also examined. Treatment of tumor cells with HHP 250 MPa for 10 min led to the significant expression of HSP70, HSP90 and CRT compared to untreated cells. Additionally, tumor cells treated by HHP and frozen in time 0H or 4H were expressing the immunogenic molecules in increased level compared to untreated cells but also significantly higher to HHP treated non frozen cells (FIG. 1C). To verify the presence of immunogenic markers on cell surface, the confocal microscopy for CRT (FIG. 1E) and HSP70 and HSP90 (data not shown) was performed.

Figure 1D:
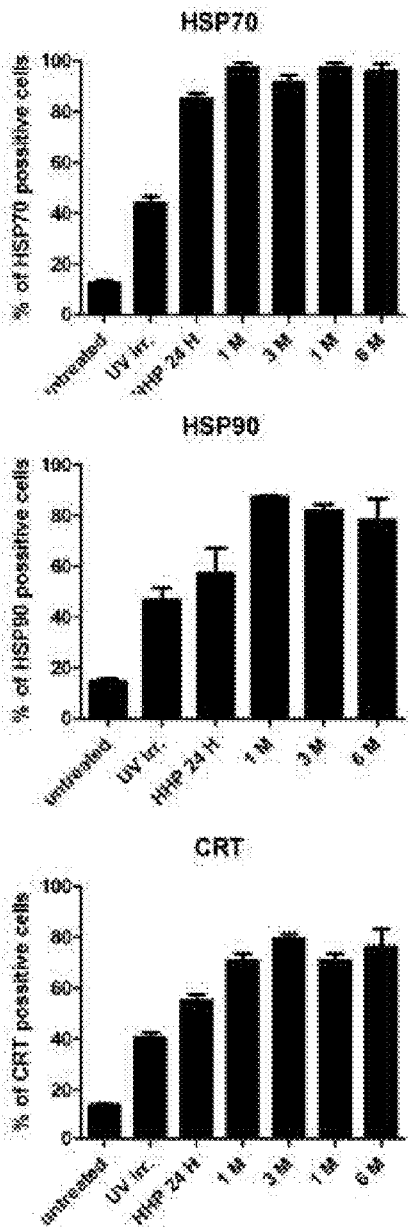
Figure 1D:
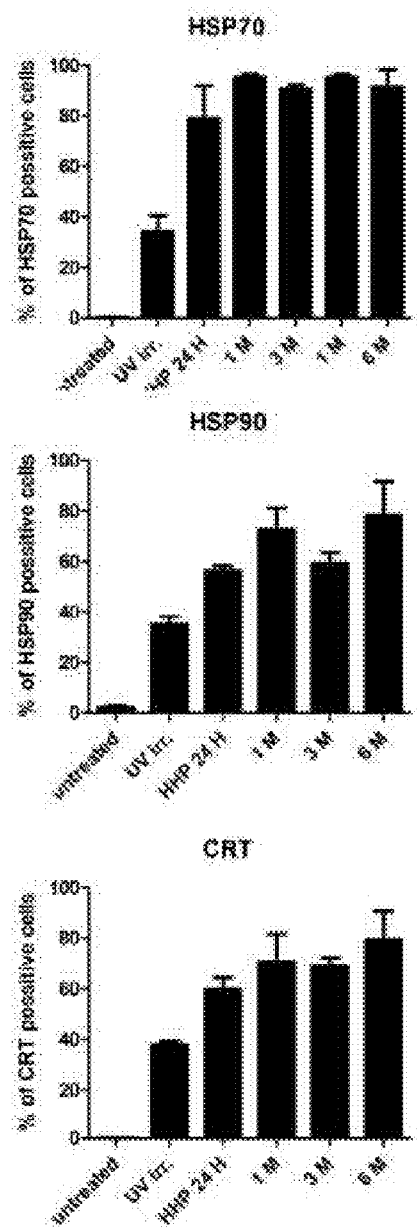
Figure 1E:
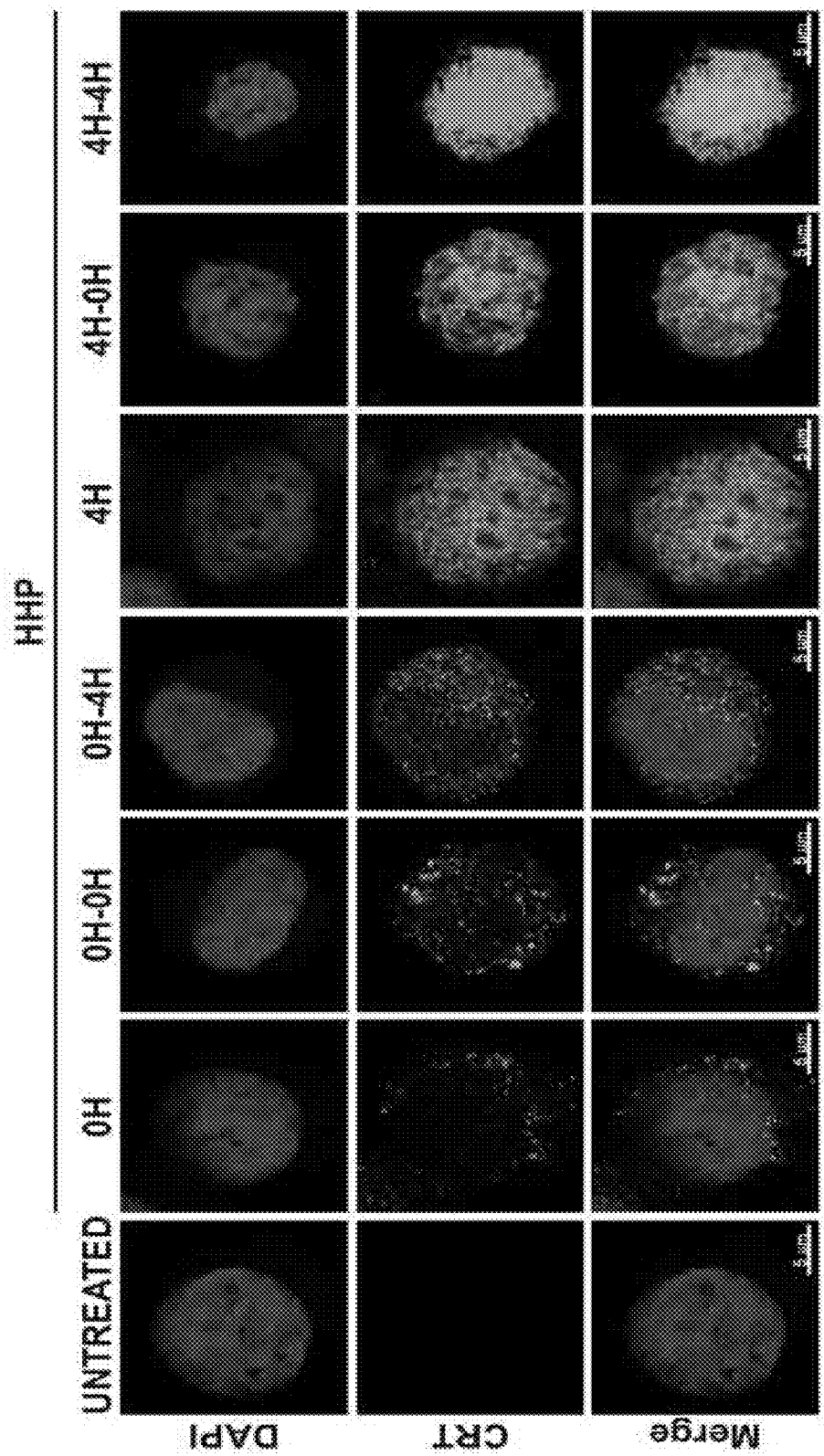

HHP-Frozen Tumor Cells are Preserving the Immunogenicity in Long Time Course:

After the initial examination of the presence of immunogenic cell death markers after HHP treatment and freezing process, the stability of expression of these markers in long time course (2 weeks, 1, 3 and 6 months) was evaluated. Expression of HSP70, HSP90 and CRT by other cancer cell lines are detected to a similar extent for 6 months (FIG. 1D).

HHP Treatment and Cryopreservation of Tumor Cells Induce Positively an Accumulation of Tumor Antigens Compared to Other Cytoskeletal Proteins:

Next, the presence of the two most expressed tumor antigens on the cell surface of prostate LNCap cell line PSA (prostate-specific antigen) and PSMA (prostate-specific membrane antigen) and the expression of Her2/Neu tumor antigen on the cell surface of SKOV3 cell line were analyzed by flow cytometry after the HHP treatment and in HHP-frozen tumor cells. Treatment of tumor cells by HHP does not influence the expression level of any mentioned tumor antigen (PSA, PSMA and Her2/Neu) (FIG. 2A). HHP-frozen tumor cells are expressing the same level of all three antigens tested in all tested times and conditions. To determine the whole amount of protein PSA and PSMA in LNCap cell line and Her2/Neu in SKOV3 cell line after the treatment of HHP and cryopreservation, Western Blot analysis was used. Compared to untreated cells, cells treated with HHP have a higher detected amount of PSA and PSMA protein (FIG. 2B, C). Furthermore, after the cryopreservation, the protein level of PSA, PSMA and Her2/Neu was significantly higher than those in untreated cells and even significantly higher than in HHP treated but non frozen cells.

HHP-Frozen Tumor Cells are Phagocytosed by DCs at the Same Level as Non-Frozen Cells:

In view of the established role of CRT as a phagocytosis-promoting signal, the rate of phagocytosis of HHP-treated and HHP-frozen prostate (LNCap) and ovarian (SKOV3) tumor cells by DCs by flow cytometry was investigated. As previously described, HHP-treated tumor cells are phagocytosed at a faster rate and to a greater extent than tumor cells killed by modifications like UV-B irradiation, photodynamic therapy by hypericin or anthracyclines. After 24 h, the rate of phagocytosis of HHP-frozen tumor cells was non-significantly higher in comparison to non-cryopreserved HHP treated cells (FIG. 3A, B).

Phagocytosis of HHP-Frozen Tumor Cells Induces the Expression of Maturation-Associated Molecules on DCs:

The ability of DCs to activate the immune response depends on their maturation status and the expression of costimulatory molecules. The phenotype of DCs that had phagocytosed prostate (LNCap) and ovarian (SKOV3) tumor cells killed by HHP and HHP-frozen was analyzed. The data demonstrates that the interaction of DCs with HHP-frozen tumor cells induce the same significant upregulation of CD80, CD83, and CD86 with subsequent maturation with polyI:C. Thus, cryopreservation of tumor cells does not negatively influence the maturation process of dendritic cells. Furthermore, cryopreservation of tumor cells does not influence viability of cells in the final product (data not shown).

DCs Pulsed with HHP-Frozen Tumor Cells Induce Tumor-Specific T Cells:

To investigate whether cryopreserved tumor cells expressing immunogenic cell death markers induce anti-tumor immunity, the ability of tumor cell-loaded DCs to activate tumor cell-specific T cell responses was evaluated. Prostate (LNCap) and ovarian (SKOV3) tumor cells killed by HHP and HHP-frozen tumor cells were cocultured with immature DCs with subsequent maturation with polyI:C. These DCs were then used as stimulators of autologous T cells, and the frequency of IFN-γ-producing T cells was analyzed 1 week later, after restimulation with tumor cell-loaded DCs. DCs pulsed with tumor cells killed by HHP induced a greater number of tumor-specific $CD4^+$ and $CD8^+$ IFN-γ-producing T cells compared to immature DCs (FIG. 4A, B). Furthermore, DCs pulsed with tumor cells killed by HHP and cryopreserved induced significantly ($*p<0.05$) greater number of tumor-specific $CD8^+$ IFN-γ-producing T cells and non-significantly increased percentage of $CD4^+$ T cells (FIG. 4A, B).

6.3 Discussion

The results show that the cryopreservation process does not abolish the immunogenicity of HHP-treated tumor cells. In particular, the results demonstrate that the cryopreserved HHP treated tumor cells express a significantly higher amount of immunogenic markers compared to non-frozen cells. The same level of expression of IMM markers HSP70 and HSP90 were detected after 2 weeks, 1, 2, and 3 months of cryo storage. The expression of CRT IMM marker was non-significantly decreased after the first month of storage. Nevertheless, the expression of IMM markers is still significantly higher compared to untreated cells during all the tested time.

The results also demonstrate that the cryopreservation of the HHP-treated tumor cells does not negatively influence the amount of tumor associated antigen. The expression of PSA, PSMA and Her2/Neu protein on the surface of HHP and HHP-frozen cells was comparable. However, the complete cell lysate of HHP-treated tumor cells contained significantly higher amount of all three tested proteins detected by western blotting. This phenomena was even increased after the cryopreservation process in both prostate and ovarian tumor cells.

The results also demonstrate that the rate of phagocytosis of HHP-frozen prostate tumor cells was comparable to HHP-treated non-frozen tumor cells. In fact, more than 85% of pulsed dendritic cells with apoptotic bodies were detected. Furthermore, the level of expression of maturation-associated markers shows the similar activation status of DCs pulsed with HHP-frozen tumor cells. Moreover, DCs pulsed with HHP-treated tumor cells efficiently stimulated tumor-specific IFN-γ-producing $CD8^+$ and $CD4^+$ T cells. However, the cryopreservation process of tumor cells significantly increased the percentage of $CD8^+$ IFN-γ-producing T cells.

The embodiments described herein are intended to be merely exemplary, and those skilled in the art will recognize, or be able to ascertain using no more than routine experimentation, numerous equivalents to the specific procedures described herein. All such equivalents are considered to be within the scope of the present invention and are covered by the following claims.

All references (including patent applications, patents, and publications) cited herein are incorporated herein by reference in their entirety and for all purposes to the same extent as if each individual publication or patent or patent application was specifically and individually indicated to be incorporated by reference in its entirety for all purposes.

What is claimed is:

1. A method for preparing a pharmaceutical composition for use in immunotherapy comprising:
   a) inducing immunogenic cell death in a population of cancer cells;
   b) cryopreserving the cancer cells undergoing immunogenic cell death in a cryopreservant, wherein the cells undergoing immunogenic cell death are cryopreserved within 2.5 hours after induction of immunogenic cell death;
   c) thawing the cryopreserved cancer cells; and
   d) preparing a pharmaceutical composition comprising the thawed cancer cells for use in immunotherapy, wherein the thawed cancer cells retain one or more of the hallmarks of immunogenic cell death.

2. The method of claim 1, wherein the cancer cells are from a cancer cell line.

3. The method of claim 1, wherein the cancer cells originate from multiple cancer cell lines.

4. The method of claim 1, wherein the immunogenic cell death is induced by high hydrostatic pressure, anthracyclines, anti-EGFR antibodies, Big Potassium channel antagonists, bortezomib, cardiac glycosides, cyclophosphamide, GADD43/PP1 inhibitors and mitomycin, irradiation by UV light or gamma rays, oxaliplatin, photodynamic therapy with hypericin, poly(I:C), or thapsigargin and cisplatin.

5. The method of claim 1, wherein the cell death is induced by high hydrostatic pressure.

6. The method of claim 1, wherein the cryopreservant contains dimethyl sulphoxide at a concentration of at least 5%.

7. The method of claim 1, wherein the cryopreservant contains glycerol at a concentration of at least 5%.

8. The method of claim 1, wherein the cells undergoing immunogenic cell death are cryopreserved at a temperature below −75° C.

9. The method of claim 1, wherein the cryopreservation is performed by slow freezing.

10. The method of claim 1, wherein the thawing is performed for between 5 seconds and 10 minutes at a temperature between 32° C. and 40° C.

11. The method of claim 1, wherein the immunotherapy is for the treatment of a solid tumor cancer.

12. The method of claim 11, wherein the solid tumor cancer is prostate cancer, ovarian cancer, lung cancer, renal cancer, colon cancer, breast cancer or glioblastoma.

13. The method of claim 1, wherein the one or more of the hallmarks of immunogenic cell death are selected from the group consisting of calreticulin, HSP70, and HSP90.

14. The method of claim 1, wherein the pharmaceutical composition comprises immature dendritic cells.

15. The method of claim 1, wherein the cells undergoing immunogenic cell death are cryopreserved within 30 minutes to 2 hours after induction of immunogenic cell death.

16. A method for preparing a pharmaceutical composition for use in immunotherapy comprising:
   a) inducing immunogenic cell death in a population of cancer cells;
   b) cryopreserving the cancer cells undergoing immunogenic cell death in a cryopreservant, wherein the cells undergoing immunogenic cell death are cryopreserved within six hours after induction of immunogenic cell death;
   c) thawing the cryopreserved cancer cells; and
   d) preparing a pharmaceutical composition comprising the thawed cancer cells for use in immunotherapy, wherein the thawed cancer cells retain one or more of the hallmarks of immunogenic cell death.

17. The method of claim 16, wherein the cells undergoing immunogenic cell death are cryopreserved within 30 minutes to 4 hours after induction of immunogenic cell death.

18. The method of claim 16, wherein the cells undergoing immunogenic cell death are cryopreserved within 1.5 hours to 2.5 hours after induction of immunogenic cell death.

19. The method of claim 16, wherein the cancer cells are from a cancer cell line.

20. The method of claim 16, wherein the cancer cells originate from multiple cancer cell lines.

21. The method of claim 16, wherein the immunogenic cell death is induced by high hydrostatic pressure, anthracyclines, anti-EGFR antibodies, Big Potassium channel antagonists, bortezomib, cardiac glycosides, cyclophosphamide, GADD43/PP1 inhibitors and mitomycin, irradiation by UV light or gamma rays, oxaliplatin, photodynamic therapy with hypericin, poly(I:C), or thapsigargin and cisplatin.

22. The method of claim 16, wherein the cell death is induced by high hydrostatic pressure.

23. The method of claim 16, wherein the cryopreservant contains dimethyl sulphoxide at a concentration of at least 5%.

24. The method of claim 16, wherein the cryopreservant contains glycerol at a concentration of at least 5%.

25. The method of claim 16, wherein the cells undergoing immunogenic cell death are cryopreserved at a temperature below −75° C.

26. The method of claim 16, wherein the cryopreservation is performed by slow freezing.

27. The method of claim 16, wherein the thawing is performed for between 5 seconds and 10 minutes at a temperature between 32° C. and 40° C.

28. The method of claim 16, wherein the immunotherapy is for the treatment of a solid tumor cancer.

29. The method of claim 28, wherein the solid tumor cancer is prostate cancer, ovarian cancer, lung cancer, renal cancer, colon cancer, breast cancer or glioblastoma.

30. The method of claim 16, wherein the one or more of the hallmarks of immunogenic cell death are selected from the group consisting of calreticulin, HSP70, and HSP90.

31. The method of claim 16, wherein the pharmaceutical composition comprises immature dendritic cells.

32. A method for preparing a pharmaceutical composition for use in immunotherapy comprising:
   a) inducing immunogenic cell death in a population of cancer cells;
   b) cryopreserving the cancer cells undergoing immunogenic cell death in a cryopreservant;
   c) thawing the cryopreserved cancer cells, wherein the thawed cells are put back into culture for at least 1 hour and not more than 6 hours before being used for the pharmaceutical preparation; and
   d) preparing a pharmaceutical composition comprising the thawed cancer cells for use in immunotherapy, wherein the thawed cancer cells retain one or more of the hallmarks of immunogenic cell death.

33. The method of claim 32, wherein the cancer cells are from a cancer cell line.

34. The method of claim 32, wherein the cancer cells originate from multiple cancer cell lines.

35. The method of claim 32, wherein the immunogenic cell death is induced by high hydrostatic pressure, anthracyclines, anti-EGFR antibodies, Big Potassium channel antagonists, bortezomib, cardiac glycosides, cyclophosphamide, GADD43/PP1 inhibitors and mitomycin, irradiation by UV light or gamma rays, oxaliplatin, photodynamic therapy with hypericin, poly(I:C), or thapsigargin and cisplatin.

36. The method of claim 32, wherein the cell death is induced by high hydrostatic pressure.

37. The method of claim 32, wherein the cryopreservant contains dimethyl sulphoxide at a concentration of at least 5%.

38. The method of claim 32, wherein the cryopreservant contains glycerol at a concentration of at least 5%.

39. The method of claim 32, wherein the cells undergoing immunogenic cell death are cryopreserved at a temperature below −75° C.

40. The method of claim 32, wherein the cryopreservation is performed by slow freezing.

41. The method of claim 32, wherein the thawing is performed for between 5 seconds and 10 minutes at a temperature between 32° C. and 40° C.

42. The method of claim 32, wherein the immunotherapy is for the treatment of a solid tumor cancer.

43. The method of claim 42, wherein the solid tumor cancer is prostate cancer, ovarian cancer, lung cancer, renal cancer, colon cancer, breast cancer or glioblastoma.

44. The method of claim 32, wherein the one or more of the hallmarks of immunogenic cell death are selected from the group consisting of calreticulin, HSP70, and HSP90.

45. The method of claim 32, wherein the pharmaceutical composition comprises immature dendritic cells.

\* \* \* \* \*